US012318210B2

(12) United States Patent
Rajagopal et al.

(10) Patent No.: US 12,318,210 B2
(45) Date of Patent: Jun. 3, 2025

(54) PREMATURE VENTRICULAR CONTRACTION (PVC) DETECTION

(71) Applicant: Medtronic, Inc., Minneapolis, MN (US)

(72) Inventors: Gautham Rajagopal, Minneapolis, MN (US); Michael L. Hudziak, Stillwater, MN (US); Shantanu Sarkar, Roseville, MN (US); Gary Toering, Oak Grove, MN (US); Jerry D. Reiland, Coon Rapids, MN (US); Yuying Chao, Vadnais Heights, MN (US); Stephanie Chen, Oakland Gardens, NY (US)

(73) Assignee: Medtronic, Inc., Minneapolis, MN (US)

( * ) Notice: Subject to any disclaimer, the term of this patent is extended or adjusted under 35 U.S.C. 154(b) by 464 days.

(21) Appl. No.: 16/436,012

(22) Filed: Jun. 10, 2019

(65) Prior Publication Data
US 2020/0383597 A1    Dec. 10, 2020

(51) Int. Cl.
*A61B 5/366* (2021.01)
*A61B 5/00* (2006.01)
(Continued)

(52) U.S. Cl.
CPC .......... *A61B 5/366* (2021.01); *A61B 5/02028* (2013.01); *A61B 5/076* (2013.01);
(Continued)

(58) Field of Classification Search
CPC . A61B 5/0472; A61B 5/02028; A61B 5/0422; A61B 5/0432; A61B 5/04525;
(Continued)

(56) References Cited

U.S. PATENT DOCUMENTS 4,531,527 A    7/1985    Reinhold, Jr. et al.
4,552,154 A    11/1985   Hartlaub
(Continued)

FOREIGN PATENT DOCUMENTS

WO    2004096353 A1    11/2004

OTHER PUBLICATIONS

Panela et al., "Neurohormonal, Structural, and Functional Recovery Pattern After Premature Ventricular Complex Ablation is Independent of Structural Heart Disease Status in Patients with Depressed Left Ventricular Ejection Fraction: A Prospective Multicenter Study," Journal of the American College of Cardiology, vol. 62, No. 13, Sep. 24, 2013, pp. 1195-1202.
(Continued)

*Primary Examiner* — Jennifer Pitrak McDonald
*Assistant Examiner* — Shreya Anjaria
(74) *Attorney, Agent, or Firm* — Shumaker & Sieffert, P.A.

(57) ABSTRACT

Techniques for determining whether a ventricular depolarization is a premature ventricular contraction (PVC) depolarization may include processing circuitry of a medical system identifying an interval from a maximum slope point to a minimum slope point for each of a plurality of ventricular depolarizations and, for each of the plurality of ventricular depolarizations as a current ventricular depolarization, determining that the intervals from the maximum slope point to the minimum slope point for the current ventricular depolarization, a preceding adjacent ventricular depolarization of the plurality of ventricular depolarizations, and a subsequent adjacent ventricular depolarization of the plurality of ventricular depolarizations satisfy one or more slope criteria. The processing circuitry determines that the current ventricular depolarization is a PVC depolarization based on the intervals from the maximum slope point to the
(Continued)

minimum slope point satisfying the one or more slope criteria.

29 Claims, 11 Drawing Sheets

(51) Int. Cl.
    *A61B 5/02*            (2006.01)
    *A61B 5/07*            (2006.01)
    *A61B 5/287*          (2021.01)
    *A61B 5/333*          (2021.01)
    *A61B 5/35*            (2021.01)

(52) U.S. Cl.
    CPC .............. *A61B 5/287* (2021.01); *A61B 5/333* (2021.01); *A61B 5/35* (2021.01); *A61B 5/686* (2013.01)

(58) Field of Classification Search
    CPC ......... A61B 5/076; A61B 5/686; A61B 5/366; A61B 5/35; A61B 5/287; A61B 5/333; A61B 5/316; A61B 5/352; A61B 5/364; G16H 40/63; G16H 40/67; G16H 50/20; A61N 1/36507; A61N 1/3627; A61N 1/3702
    See application file for complete search history.

(56) References Cited

U.S. PATENT DOCUMENTS

| | | | |
|---|---|---|---|
| 5,159,932 | A | 11/1992 | Zanetti et al. |
| 6,453,192 | B1 | 9/2002 | Ding et al. |
| 6,954,671 | B1 | 10/2005 | Hoijer et al. |
| 7,027,858 | B2 * | 4/2006 | Cao ..................... A61B 5/0456 600/521 |
| 7,751,876 | B2 * | 7/2010 | Healey ................. A61B 5/0468 600/517 |
| 7,778,699 | B1 | 8/2010 | Ferrise et al. |
| 8,027,722 | B1 | 9/2011 | Nabutovsky |
| 8,380,294 | B2 | 2/2013 | Messier et al. |
| 8,457,728 | B2 | 6/2013 | Schneider et al. |
| 8,704,688 | B2 | 4/2014 | Shen et al. |
| 8,855,755 | B2 * | 10/2014 | Zhang ................. A61B 5/0464 600/516 |
| 8,989,852 | B2 | 3/2015 | Gill et al. |
| 9,427,594 | B1 * | 8/2016 | Bornzin ............. A61N 1/37288 |
| 9,492,138 | B2 | 11/2016 | Kapoor |
| 9,675,270 | B2 * | 6/2017 | Sarkar ................. A61B 5/0468 |
| 9,706,938 | B2 | 7/2017 | Chakravarthy et al. |
| 9,936,890 | B2 | 4/2018 | Sarkar |
| 9,968,274 | B2 | 5/2018 | Korzinov et al. |
| 10,779,744 | B2 | 9/2020 | Rapin et al. |
| 11,234,629 | B2 | 2/2022 | Liu et al. |
| 2007/0255345 | A1 | 11/2007 | Krause |
| 2010/0274148 | A1 | 10/2010 | Zhang et al. |
| 2012/0277608 | A1 | 11/2012 | Schneider et al. |
| 2014/0107723 | A1 * | 4/2014 | Hou ..................... A61N 1/3756 607/9 |
| 2014/0276928 | A1 | 9/2014 | Vanderpool et al. |
| 2015/0335894 | A1 * | 11/2015 | Bornzin ............... A61N 1/3756 607/18 |
| 2016/0135706 | A1 | 5/2016 | Sullivan et al. |
| 2016/0310029 | A1 | 10/2016 | Sarkar |
| 2016/0310031 | A1 * | 10/2016 | Sarkar ..................... A61B 5/287 |
| 2017/0119274 | A1 | 5/2017 | Chakravarthy et al. |
| 2018/0303345 | A1 | 10/2018 | Adler |
| 2019/0051393 | A1 | 2/2019 | Whiting et al. |
| 2019/0216350 | A1 | 7/2019 | Sullivan et al. |
| 2019/0336032 | A1 | 11/2019 | Gill et al. |
| 2020/0237314 | A1 | 7/2020 | Qu et al. |
| 2020/0357519 | A1 | 11/2020 | Chakravarthy et al. |

OTHER PUBLICATIONS

Alqarawi et al., "Identifying and Managing Premature Ventricular Contraction-Induced Cardiomyopathy: What, Why, and How?," Canadian Journal of Cardiology, vol. 33, Feb. 2017, pp. 287-290.
Callans, "Premature Ventricular Contraction-induced Cardiomyopathy," Arrhythmia & Electrophysiology Review, vol. 6, Dec. 2017, pp. 153-155.
Panela et al., "Clinical recognition of pure premature ventricular complex-induced cardiomyopathy at presentation," Heart Rhythm Society, vol. 14, No. 12, Dec. 2017, pp. 1864-1870.
Panela et al., "Ablation of frequent PVC in patients meeting criteria for primary prevention ICD implant: Safety of withholding the implant," Heart Rhythm Society, vol. 12, No. 12, Dec. 2015, pp. 2434-2442.
Talbi, M. L. et al., "PVC discrimination using the QRS power spectrum and self-organizing maps," Computer Methods and Programs in Biomedicine, Elsevier, Masterdam, NL, vol. 94, No. 3, Jun. 1, 2009, pp. 223-231.
PCT/US2020/028054, PCT The International Search Report and Written Opinion, mailed Jul. 2, 0220, 10pages.
U.S. Appl. No. 16/921,346, filed Jul. 6, 2020, by Burnes et al.
Cho et al., "PVC Classification Algorithm Through Efficient R Wave Detection," Journal of Sensor Science and Technology, vol. 22, No. 5, Sep. 30, 2013, pp. 338-345.
Rodrigues De Oliveira et al., , "Geometrical Features for Premature Ventricular Contraction Recognition with Analytic Hierarchy Process Based Machine Learning Algorithms Selection," Computer Methods and Programs in Biomedicine, vol. 169, Feb. 1, 2019, pp. 59-69.
Office Action from U.S. Appl. No. 16/921,346, dated Dec. 30, 2021, 15 pp.
Response to Office Action dated Dec. 30, 2021, from U.S. Appl. No. 16/921,346, filed Mar. 30, 2022, 12 pp.
Advisory Action from U.S. Appl. No. 16/921,346 dated Aug. 5, 2022, 3 pp.
Final Office Action from U.S. Appl. No. 16/921,346, dated May 27, 2022, 10 pp.
Kaya et al., "Classification of Premature Ventricular Contraction in ECG", International Journal of Advanced Computer Science and Applications, vol. 6, No. 7, 2015, pp. 34-40, Retrieved from the Internet on Jan. 31, 2023 from URL: https://avesis.ktu.edu.tr/yayin/9437012c-c146-4e8a-a482-1cc8653890a6/classification-of-premature-ventricular-contraction-in-ecg.
Mazidi et al., "Detection of premature ventricular contraction (PVC) using linear and nonlinear techniques: an experimental study", Cluster Computing, vol. 23, No. 2, Springer Science+Business Media, LLC, Jul. 11, 2019, pp. 759-774, URL: https://link.springer.com/article/10.1007/s10586-019-02953-x.
Office Action from U.S. Appl. No. 16/921,346 dated Nov. 22, 2022, 10 pp.
Response to Final Office Action dated May 27, 2022 from U.S. Appl. No. 16/921,346, filed Jul. 27, 2022, 12 pp.
U.S. Appl. No. 18/050,814, filed Oct. 28, 2022, naming inventors Rajagopal et al.
Zhang et al., "Premature Ventricular Contractions' Detection Based on Active Learning", Scientific Programming, vol. 2021, Mar. 8, 2021, 14 pp., URL: https://www.hindawi.com/journals/sp/2021/5556011/.
Zhou, "Automatic Detection of Premature Ventricular Contraction Using Quantum Neural Networks", Automatic detection of premature Third IEEE Symposium on Bioinformatics and Bioengineering, IEEE, Mar. 12, 2003, pp. 169-173, URL: https://citeseerx.ist.psu.edu/viewdoc/download?doi=10.1.1.138.1032&rep=rep1&type=pdf.
Response to Office Action dated Nov. 22, 2022 from U.S. Appl. No. 16/921,346, filed Feb. 22, 2023, 13 pp.

* cited by examiner

PREMATURE VENTRICULAR CONTRACTION (PVC) DETECTION

FIELD

The disclosure relates generally to medical device systems and, more particularly, medical device systems configured to detect premature ventricular contractions (PVCs).

BACKGROUND

Medical devices may be used to monitor physiological signals of a patient. For example, some medical devices are configured to sense cardiac electrogram (EGM) signals indicative of the electrical activity of the heart via electrodes. Some medical devices may be configured to deliver a therapy in conjunction with or separate from the monitoring of physiological signals.

PVCs are premature heartbeats originating from the ventricles of the heart. PVCs are premature because they occur before the regular heartbeat originating from the sinoatrial node. During a PVC event, the ventricles electrically discharge and contract prematurely before the normal electrical discharge arrives from the sinoatrial node. PVCs may occur in healthy individuals. PVCs may be caused by caffeine, smoking, alcohol consumption, stress, exhaustion, pharmacological toxicity, electrolyte imbalance, lack of oxygen, and heart attack as examples. Common symptoms associated with PVCs include palpitations, dizziness, fatigue, dyspnea, chest pain, and lightheadedness. PVCs are normally considered benign, but may potentially cause cardiomyopathy, ventricular arrythmias, and heart failure.

Management strategies for PVC induced cardiomyopathy include medical therapy and catheter ablation, with an increasing role for catheter ablation in view of the potential for permanent suppression of PVCs. Ablation to suppress PVCs may lead to improvement of left ventricular systolic dysfunction (LVSD) and normalization of left ventricular ejection fraction (LVEF). PVC burden, i.e., a quantification of the amount of PVCs over a period of time, can be an independent predictor of PVC induced cardiomyopathy. Presently, 24-hour Holter monitoring is the most commonly used method to determine PVC burden.

SUMMARY

In general, this disclosure is directed to techniques for detecting PVCs using a medical device to, for example, facilitate a determination of PVC burden. More particularly, the disclosure is directed to techniques for evaluating ventricular depolarizations in a cardiac EGM to determine whether they are PVC depolarizations. Processing circuitry may determine that a ventricular depolarization is a PVC depolarization based on satisfaction of one or more criteria, including criteria related to inter-depolarization intervals indicative of depolarization rate (e.g., R-R intervals) or criteria related to the morphology of the depolarizations in the cardiac EGM.

For some medical devices, e.g., those utilizing external, subcutaneous, or other extra-vascular electrodes, the location and orientation of the electrodes used to sense the cardiac EGM relative to the heart and other tissue may vary between patients, and within a given patient over time. As a consequence, the morphology of depolarizations may vary, and noise may be introduced into the cardiac EGM. The criteria used by the processing circuitry to determine whether a given depolarization is a PVC according to the techniques of this disclosure facilitate sensitivity and specificity of PVC detection under such conditions, which may facilitate more accurate determinations of PVC burden, cardiac wellness, and risk of sudden cardiac death, and may lead to clinical interventions to suppress PVCs such as medications and PVC ablations.

In some examples, processing circuitry may use noise criteria to avoid classifying noisy depolarizations in the cardiac EGM as PVC depolarizations. In some examples, the morphological criteria include one or more slope criteria, and processing circuitry may consider whether intervals between maximum and minimum slope points in depolarizations satisfy the slope criteria. Instead of, or in addition to, the slope criteria, the morphological criteria for identifying PVC depolarizations may include one or more correlation criteria to which processing circuitry may compare correlation values between depolarization. The processing circuitry may use a cross-correlation technique, a difference sum technique, or other techniques to determine the correlation values. In some examples, the correlation criteria may include one or more thresholds that are adjustable based on a maximum amount of correlation between depolarizations, e.g., a maximum cross-correlation value or a minimum difference sum value, during an update period preceding the current depolarization under consideration.

In one example, a medical system comprises a plurality of electrodes configured to sense a cardiac electrogram of a patient, and processing circuitry. The processing circuitry is configured to identify a plurality of ventricular depolarizations within the cardiac electrogram, and for each of the plurality of ventricular depolarizations, identify a maximum slope point, a minimum slope point, and an interval from the maximum slope point to the minimum slope point. The processing circuitry is further configured to, for each of the plurality ventricular depolarizations as a current ventricular depolarization, determine that the intervals from the maximum slope point to the minimum slope point for the current ventricular depolarization, a preceding adjacent ventricular depolarization of the plurality of ventricular depolarizations, and a subsequent adjacent ventricular depolarization of the plurality of ventricular depolarizations satisfy one or more slope criteria, and determine that the current ventricular depolarization is a premature ventricular contraction (PVC) depolarization based on the intervals from the maximum slope point to the minimum slope point satisfying the one or more slope criteria.

In another example, a method comprises sensing a cardiac electrogram of a patient via a plurality of electrodes and identifying a plurality of ventricular depolarizations within the cardiac electrogram. The method further comprises for each of the plurality of ventricular depolarizations, identifying a maximum slope point, a minimum slope point, and an interval from the maximum slope point to the minimum slope point. The method further comprises, for each of the plurality ventricular depolarizations as a current ventricular depolarization, determining that the intervals from the maximum slope point to the minimum slope point for the current ventricular depolarization, a preceding adjacent ventricular depolarization of the plurality of ventricular depolarizations, and a subsequent adjacent ventricular depolarization of the plurality of ventricular depolarizations satisfy one or more slope criteria, and determining that the current ventricular depolarization is a premature ventricular contraction (PVC) depolarization based on the intervals from the maximum slope point to the minimum slope point satisfying the one or more slope criteria.

In another example, a medical system comprises a plurality of electrodes configured to sense a cardiac electrogram of a patient, and processing circuitry. The processing circuitry is configured to identify a plurality of ventricular depolarizations within the cardiac electrogram. For each of the plurality ventricular depolarizations as a current ventricular depolarization, the processing circuitry is configured to determine a correlation value between each pairing of one of the current ventricular depolarization, a preceding adjacent ventricular depolarization, and a subsequent adjacent ventricular depolarization and another of the preceding adjacent ventricular depolarization, the current ventricular depolarization, and the subsequent adjacent ventricular depolarization. The processing circuitry is further configured to determine that the correlation values satisfy one or more correlation criteria comprising one or more thresholds and determine that the current ventricular depolarization is a premature ventricular contraction (PVC) depolarization based on the correlation values satisfying the one or more correlation criteria. The processing circuitry is further configured to, for a plurality of correlation values determined during an update period preceding the current depolarization, identify one of the plurality of correlation values representing a maximum amount of correlation among the plurality of correlation values, and adjust the one or more thresholds based on the identified one of the plurality of correlation values.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

BRIEF DESCRIPTION OF THE DRAWINGS

Like reference characters denote like elements throughout the description and figures.

DETAILED DESCRIPTION

Figure 1:
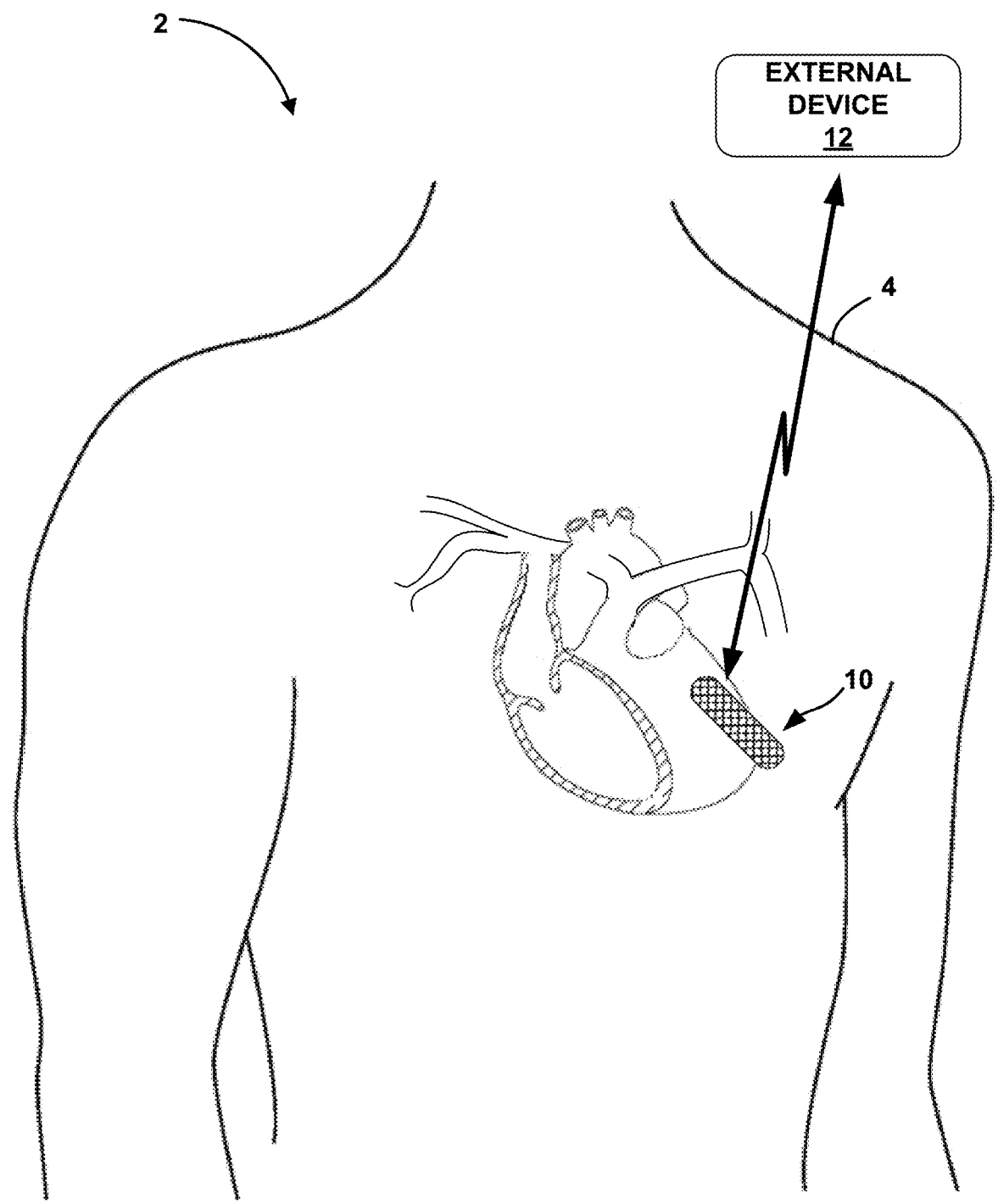
FIG. 1 illustrates the environment of an example medical system in conjunction with a patient.

A variety of types of medical devices sense cardiac EGMs. Some medical devices that sense cardiac EGMs are non-invasive, e.g., using a plurality of electrodes placed in contact with external portions of the patient, such as at various locations on the skin of the patient. The electrodes used to monitor the cardiac EGM in these non-invasive processes may be attached to the patient using an adhesive, strap, belt, or vest, as examples, and electrically coupled to a monitoring device, such as an electrocardiograph, Holter monitor, or other electronic device. The electrodes are configured to sense electrical signals associated with the electrical activity of the heart or other cardiac tissue of the patient, and to provide these sensed electrical signals to the electronic device for further processing and/or display of the electrical signals. The non-invasive devices and methods may be utilized on a temporary basis, for example to monitor a patient during a clinical visit, such as during a doctor's appointment, or for example for a predetermined period of time, for example for one day (twenty-four hours), or for a period of several days.

External devices that may be used to non-invasively sense and monitor cardiac EGMs include wearable devices with electrodes configured to contact the skin of the patient, such as patches, watches, or necklaces. One example of a wearable physiological monitor configured to sense a cardiac EGM is the SEEQ™ Mobile Cardiac Telemetry System, available from Medtronic plc, of Dublin, Ireland. Such external devices may facilitate relatively longer-term monitoring of patients during normal daily activities, and may periodically transmit collected data to a network service, such as the Medtronic Carelink™ Network.

Some implantable medical devices (IMDs) also sense and monitor cardiac EGMs. The electrodes used by IMDs to sense cardiac EGMs are typically integrated with a housing of the IMD and/or coupled to the IMD via one or more elongated leads. Example IMDs that monitor cardiac EGMs include pacemakers and implantable cardioverter-defibrillators, which may be coupled to intravascular or extravascular leads, as well as pacemakers with housings configured for implantation within the heart, which may be leadless. An example of pacemaker configured for intracardiac implantation is the Micra™ Transcatheter Pacing System, available from Medtronic plc. Some IMDs that do not provide therapy, e.g., implantable patient monitors, sense cardiac EGMs. One example of such an IMD is the Reveal LINQ™ Insertable Cardiac Monitor, available from Medtronic plc, which may be inserted subcutaneously. Such IMDs may facilitate relatively longer-term monitoring of patients during normal daily activities, and may periodically transmit collected data to a network service, such as the Medtronic Carelink™ Network.

Any medical device configured to sense a cardiac EGM via implanted or external electrodes, including the examples identified herein, may implement the techniques of this disclosure for evaluating ventricular depolarizations in a cardiac EGM to determine whether they are PVC depolarizations, which may facilitate determination of PVC burden. The techniques include evaluation of the cardiac EGM using criteria configured to provide a desired sensitivity and specificity of PVC detection despite noise and depolarization morphology variations due to varying electrode positions. The techniques of this disclosure for identifying PVC depolarizations may facilitate determinations of PVC burden, cardiac wellness, and risk of sudden cardiac death, and may lead to clinical interventions to suppress PVCs such as medications and PVC ablations.

FIG. 1 illustrates the environment of an example medical system 2 in conjunction with a patient 4, in accordance with one or more techniques of this disclosure. The example techniques may be used with an IMD 10, which may be in wireless communication with at least one of external device 12 and other devices not pictured in FIG. 1. In some examples, IMD 10 is implanted outside of a thoracic cavity of patient 4 (e.g., subcutaneously in the pectoral location illustrated in FIG. 1). IMD 10 may be positioned near the sternum near or just below the level of the heart of patient 4, e.g., at least partially within the cardiac silhouette. IMD 10 includes a plurality of electrodes (not shown in FIG. 1), and is configured to sense a cardiac EGM via the plurality of electrodes. In some examples, IMD 10 takes the form of the LINQ™ ICM, or another ICM similar to, e.g., a version or modification of, the LINQ™ ICM.

External device 12 may be a computing device with a display viewable by the user and an interface for providing input to external device 12 (i.e., a user input mechanism). In some examples, external device 12 may be a notebook computer, tablet computer, workstation, one or more servers, cellular phone, personal digital assistant, or another computing device that may run an application that enables the computing device to interact with IMD 10. External device 12 is configured to communicate with IMD 10 and, optionally, another computing device (not illustrated in FIG. 1), via wireless communication. External device 12, for example, may communicate via near-field communication technologies (e.g., inductive coupling, NFC or other communication technologies operable at ranges less than 10-20 cm) and far-field communication technologies (e.g., RF telemetry according to the 802.11 or Bluetooth® specification sets, or other communication technologies operable at ranges greater than near-field communication technologies).

External device 12 may be used to configure operational parameters for IMD 10. External device 12 may be used to retrieve data from IMD 10. The retrieved data may include values of physiological parameters measured by IMD 10, indications of episodes of arrhythmia or other maladies detected by IMD 10, and physiological signals recorded by IMD 10. For example, external device 12 may retrieve information related to detection of PVCs by IMD 10, such as a count or other quantification of PVCs, e.g., over a time period since the last retrieval of information by external device. External device 12 may also retrieve cardiac EGM segments recorded by IMD 10, e.g., due to IMD 10 determining that an episode of arrhythmia or another malady occurred during the segment, or in response to a request to record the segment from patient 4 or another user. As discussed in greater detail below with respect to FIG. 5, one or more remote computing devices may interact with IMD 10 in a manner similar to external device 12, e.g., to program IMD 10 and/or retrieve data from IMD 10, via a network.

Processing circuitry of medical system 2, e.g., of IMD 10, external device 12, and/or of one or more other computing devices, may be configured to perform the example techniques of this disclosure for determining whether a depolarization is a PVC depolarization. In some examples, the processing circuitry of medical system 2 analyzes a cardiac EGM sensed by IMD 10 to determine whether a current depolarization is a PVC depolarization based on whether the current depolarization and adjacent depolarizations in the cardiac EGM, e.g., comparisons between these depolarizations, satisfy a plurality of criteria. The criteria may include noise criteria, inter-depolarization interval (e.g., R-R interval) criteria, and/or morphological criteria, as described in greater detail below. Although described in the context of examples in which IMD 10 that senses the cardiac EGM comprises an insertable cardiac monitor, example systems including one or more implantable or external devices of any type configured to sense a cardiac EGM may be configured to implement the techniques of this disclosure.

Figure 2:
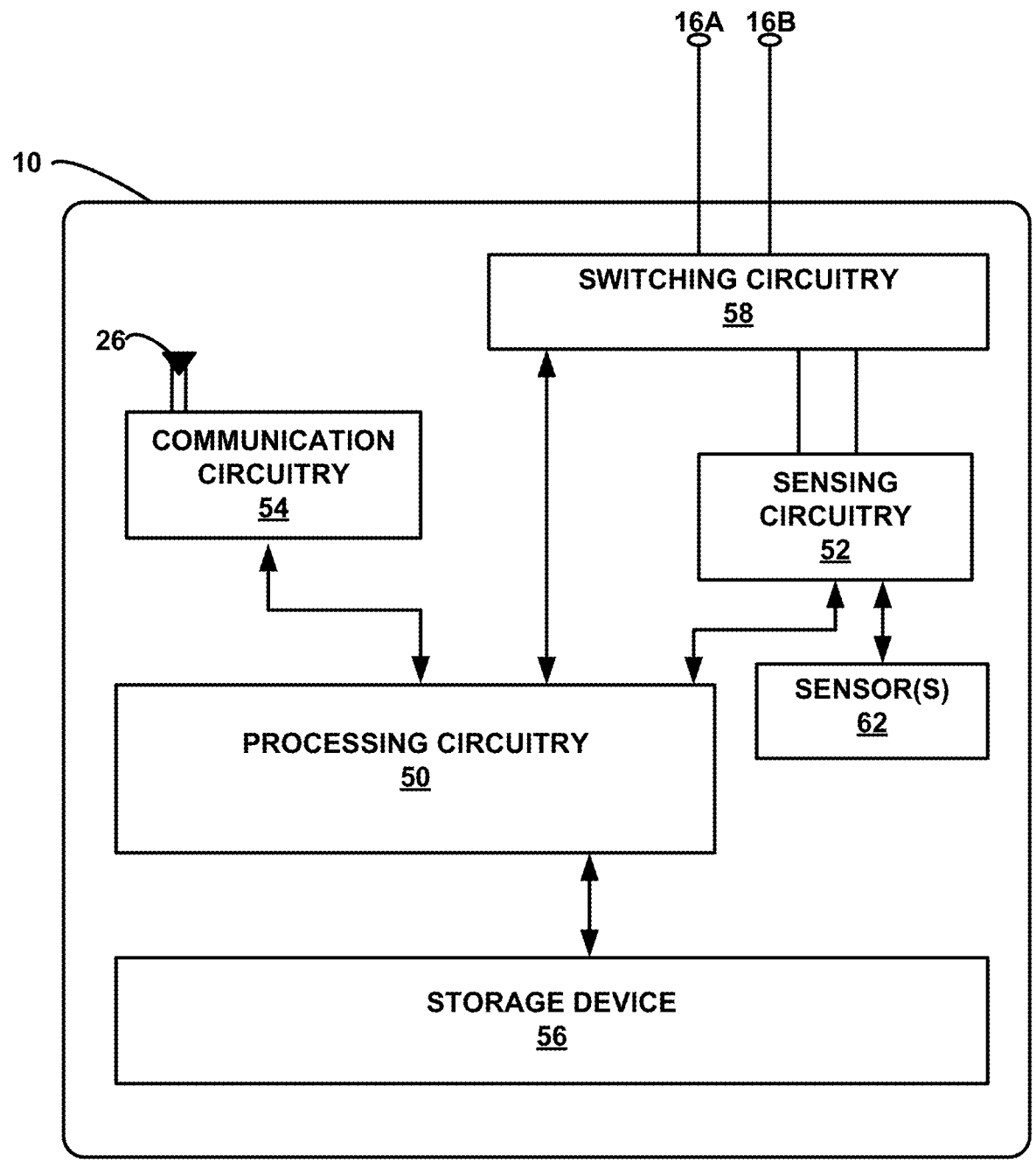
FIG. 2 is a functional block diagram illustrating an example configuration of the implantable medical device (IMD) of the medical system of FIG. 1.

FIG. 2 is a functional block diagram illustrating an example configuration of IMD 10 of FIG. 1 in accordance with one or more techniques described herein. In the illustrated example, IMD 10 includes electrodes 16A and 16B (collectively "electrodes 16"), antenna 26, processing circuitry 50, sensing circuitry 52, communication circuitry 54, storage device 56, switching circuitry 58, and sensors 62. Although the illustrated example includes two electrodes 16, IMDs including or coupled to more than two electrodes 16 may implement the techniques of this disclosure in some examples.

Processing circuitry 50 may include fixed function circuitry and/or programmable processing circuitry. Processing circuitry 50 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 50 may include multiple components, such as any combination of one or more microprocessors, one or more controllers, one or more DSPs, one or more ASICs, or one or more FPGAs, as well as other discrete or integrated logic circuitry. The functions attributed to processing circuitry 50 herein may be embodied as software, firmware, hardware or any combination thereof.

Sensing circuitry 52 may be selectively coupled to electrodes 16 via switching circuitry 58, e.g., to select the electrodes 16 and polarity, referred to as the sensing vector, used to sense a cardiac EGM, as controlled by processing circuitry 50. Sensing circuitry 52 may sense signals from electrodes 16, e.g., to produce a cardiac EGM, in order to facilitate monitoring the electrical activity of the heart. Sensing circuitry 52 also may monitor signals from sensors 62, which may include one or more accelerometers, pressure sensors, and/or optical sensors, as examples. In some examples, sensing circuitry 52 may include one or more filters and amplifiers for filtering and amplifying signals received from electrodes 16 and/or sensors 62.

Sensing circuitry 52 and/or processing circuitry 50 may be configured to detect cardiac depolarizations (e.g., P-waves of atrial depolarizations or R-waves of ventricular depolarizations) when the cardiac EGM amplitude crosses a sensing threshold. For cardiac depolarization detection, sensing circuitry 52 may include a rectifier, filter, amplifier, comparator, and/or analog-to-digital converter, in some examples. In some examples, sensing circuitry 52 may output an indication to processing circuitry 50 in response to sensing of a cardiac depolarization. In this manner, processing circuitry 50 may receive detected cardiac depolarization indicators corresponding to the occurrence of detected R-waves and P-waves in the respective chambers of heart. Processing circuitry 50 may use the indications of detected R-waves and P-waves for determining inter-depolarization intervals, heart rate, and detecting arrhythmias, such as tachyarrhythmias and asystole.

Sensing circuitry 52 may also provide one or more digitized cardiac EGM signals to processing circuitry 50 for analysis, e.g., for use in cardiac rhythm discrimination, and/or for analysis to determine whether one or more PVC detection criteria are satisfied according to the techniques of this disclosure. In some examples, processing circuitry 50 may store the digitized cardiac EGM in storage device 56. Processing circuitry 50 of IMD 10, and/or processing circuitry of another device that retrieves data from IMD 10, may analyze the cardiac EGM to determine whether one or more PVC detection criteria are satisfied according to the techniques of this disclosure.

Communication circuitry 54 may include any suitable hardware, firmware, software or any combination thereof for communicating with another device, such as external device 12, another networked computing device, or another IMD or sensor. Under the control of processing circuitry 50, communication circuitry 54 may receive downlink telemetry from, as well as send uplink telemetry to external device 12 or another device with the aid of an internal or external antenna, e.g., antenna 26. In addition, processing circuitry 50 may communicate with a networked computing device via an external device (e.g., external device 12) and a computer network, such as the Medtronic CareLink® Network. Antenna 26 and communication circuitry 54 may be configured to transmit and/or receive signals via inductive coupling, electromagnetic coupling, Near Field Communication (NFC), Radio Frequency (RF) communication, Bluetooth®, WiFi, or other proprietary or non-proprietary wireless communication schemes.

In some examples, storage device 56 includes computer-readable instructions that, when executed by processing circuitry 50, cause IMD 10 and processing circuitry 50 to perform various functions attributed to IMD 10 and processing circuitry 50 herein. Storage device 56 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media. Storage device 56 may store, as examples, programmed values for one or more operational parameters of IMD 10 and/or data collected by IMD 10 for transmission to another device using communication circuitry 54. Data stored by storage device 56 and transmitted by communication circuitry 54 to one or more other devices may include PVC detection quantifications and/or digitized cardiac EGMs, as examples.

Figure 3:
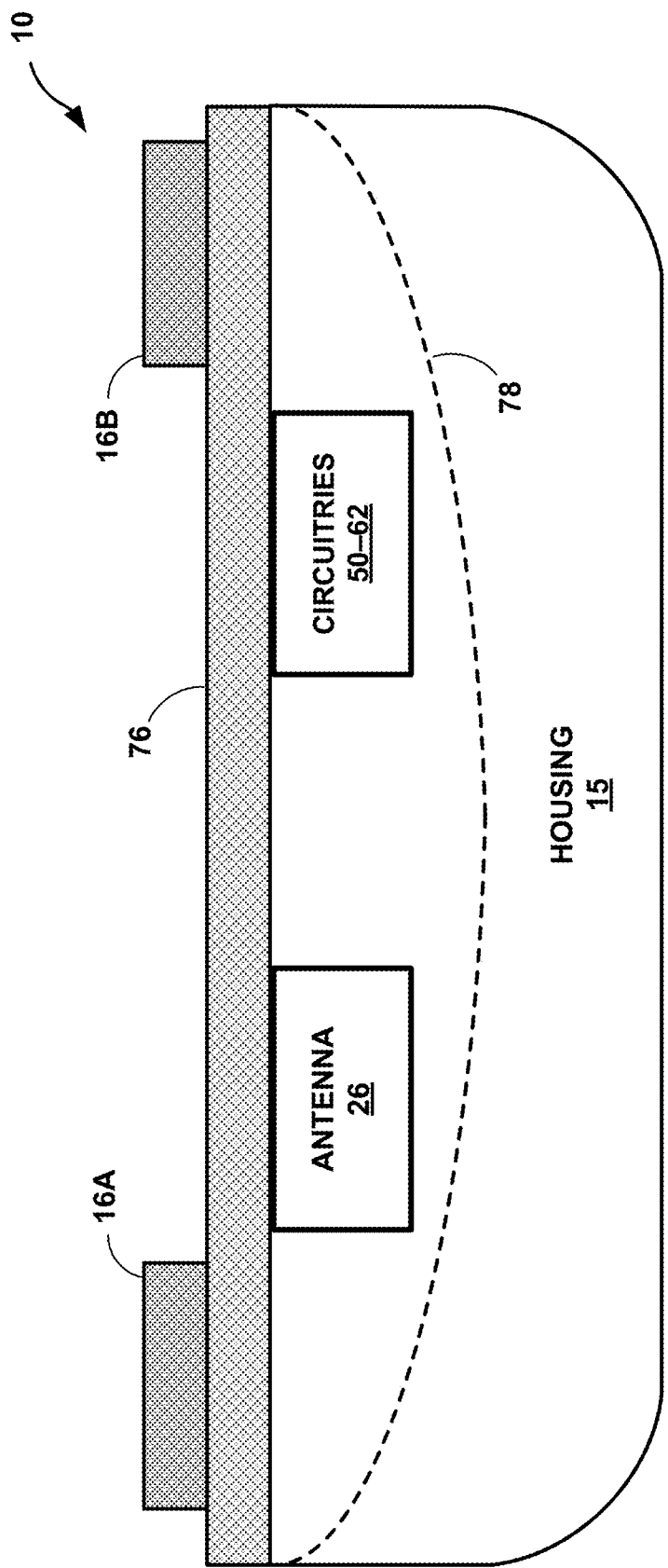
FIG. 3 is a conceptual side-view diagram illustrating an example configuration of the IMD of FIGS. 1 and 2.

FIG. 3 is a conceptual side-view diagram illustrating an example configuration of IMD 10 of FIGS. 1 and 2. In the example shown in FIG. 3, IMD 10 may include a leadless, subcutaneously-implantable monitoring device having a housing 15 and an insulative cover 76. Electrode 16A and electrode 16B may be formed or placed on an outer surface of cover 76. Circuitries 50-62, described above with respect to FIG. 2, may be formed or placed on an inner surface of cover 76, or within housing 15. In the illustrated example, antenna 26 is formed or placed on the inner surface of cover 76, but may be formed or placed on the outer surface in some examples. In some examples, one or more of sensors 62 may be formed or placed on the outer surface of cover 76. In some examples, insulative cover 76 may be positioned over an open housing 15 such that housing 15 and cover 76 enclose antenna 26 and circuitries 50-62, and protect the antenna and circuitries from fluids such as body fluids.

One or more of antenna 26 or circuitries 50-62 may be formed on the inner side of insulative cover 76, such as by using flip-chip technology. Insulative cover 76 may be flipped onto a housing 15. When flipped and placed onto housing 15, the components of IMD 10 formed on the inner side of insulative cover 76 may be positioned in a gap 78 defined by housing 15. Electrodes 16 may be electrically connected to switching circuitry 58 through one or more vias (not shown) formed through insulative cover 76. Insulative cover 76 may be formed of sapphire (i.e., corundum), glass, parylene, and/or any other suitable insulating material. Housing 15 may be formed from titanium or any other suitable material (e.g., a biocompatible material). Electrodes 16 may be formed from any of stainless steel, titanium, platinum, iridium, or alloys thereof. In addition, electrodes 16 may be coated with a material such as titanium nitride or fractal titanium nitride, although other suitable materials and coatings for such electrodes may be used.

Figure 4:
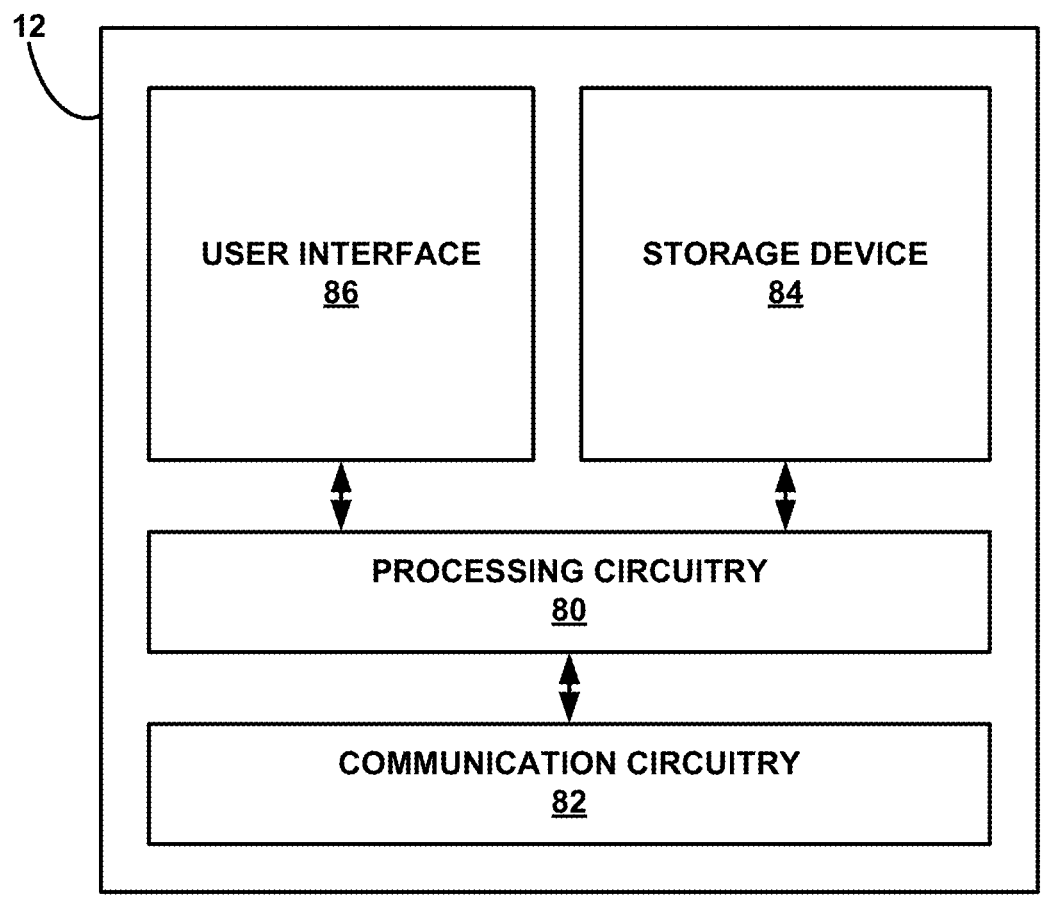
FIG. 4 is a functional block diagram illustrating an example configuration of the external device of FIG. 1.

FIG. 4 is a block diagram illustrating an example configuration of components of external device 12. In the example of FIG. 4, external device 12 includes processing circuitry 80, communication circuitry 82, storage device 84, and user interface 86.

Processing circuitry 80 may include one or more processors that are configured to implement functionality and/or process instructions for execution within external device 12. For example, processing circuitry 80 may be capable of processing instructions stored in storage device 84. Processing circuitry 80 may include, for example, microprocessors, DSPs, ASICs, FPGAs, or equivalent discrete or integrated logic circuitry, or a combination of any of the foregoing devices or circuitry. Accordingly, processing circuitry 80 may include any suitable structure, whether in hardware, software, firmware, or any combination thereof, to perform the functions ascribed herein to processing circuitry 80.

Communication circuitry 82 may include any suitable hardware, firmware, software or any combination thereof for communicating with another device, such as IMD 10. Under the control of processing circuitry 80, communication circuitry 82 may receive downlink telemetry from, as well as send uplink telemetry to, IMD 10, or another device. Communication circuitry 82 may be configured to transmit or receive signals via inductive coupling, electromagnetic coupling, Near Field Communication (NFC), Radio Frequency (RF) communication, Bluetooth®, WiFi, or other proprietary or non-proprietary wireless communication schemes. Communication circuitry 82 may also be configured to communicate with devices other than IMD 10 via any of a variety of forms of wired and/or wireless communication and/or network protocols.

Storage device 84 may be configured to store information within external device 12 during operation. Storage device 84 may include a computer-readable storage medium or computer-readable storage device. In some examples, storage device 84 includes one or more of a short-term memory or a long-term memory. Storage device 84 may include, for example, RAM, DRAM, SRAM, magnetic discs, optical discs, flash memories, or forms of EPROM or EEPROM. In some examples, storage device 84 is used to store data indicative of instructions for execution by processing circuitry 80. Storage device 84 may be used by software or applications running on external device 12 to temporarily store information during program execution.

Data exchanged between external device 12 and IMD 10 may include operational parameters. External device 12 may transmit data including computer readable instructions which, when implemented by IMD 10, may control IMD 10 to change one or more operational parameters and/or export collected data. For example, processing circuitry 80 may transmit an instruction to IMD 10 which requests IMD 10 to export collected data (e.g., PVC detection data and/or digitized cardiac EGMs) to external device 12. In turn, external device 12 may receive the collected data from IMD 10 and store the collected data in storage device 84. Processing circuitry 80 may implement any of the techniques described herein to analyze cardiac EGMs received from IMD 10, e.g., to determine whether ventricular depolarizations are PVC depolarizations.

A user, such as a clinician or patient 4, may interact with external device 12 through user interface 86. User interface 86 includes a display (not shown), such as a liquid crystal display (LCD) or a light emitting diode (LED) display or other type of screen, with which processing circuitry 80 may present information related to IMD 10, e.g., cardiac EGMs, indications of detections of PVCs, and quantifications of detected PVCs, such as a quantification of PVC burden. In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate through user interfaces presented by processing circuitry 80 of external device 12 and provide input. In other examples, user interface 86 also includes audio circuitry for providing audible notifications, instructions or other sounds to the user, receiving voice commands from the user, or both.

Figure 5:
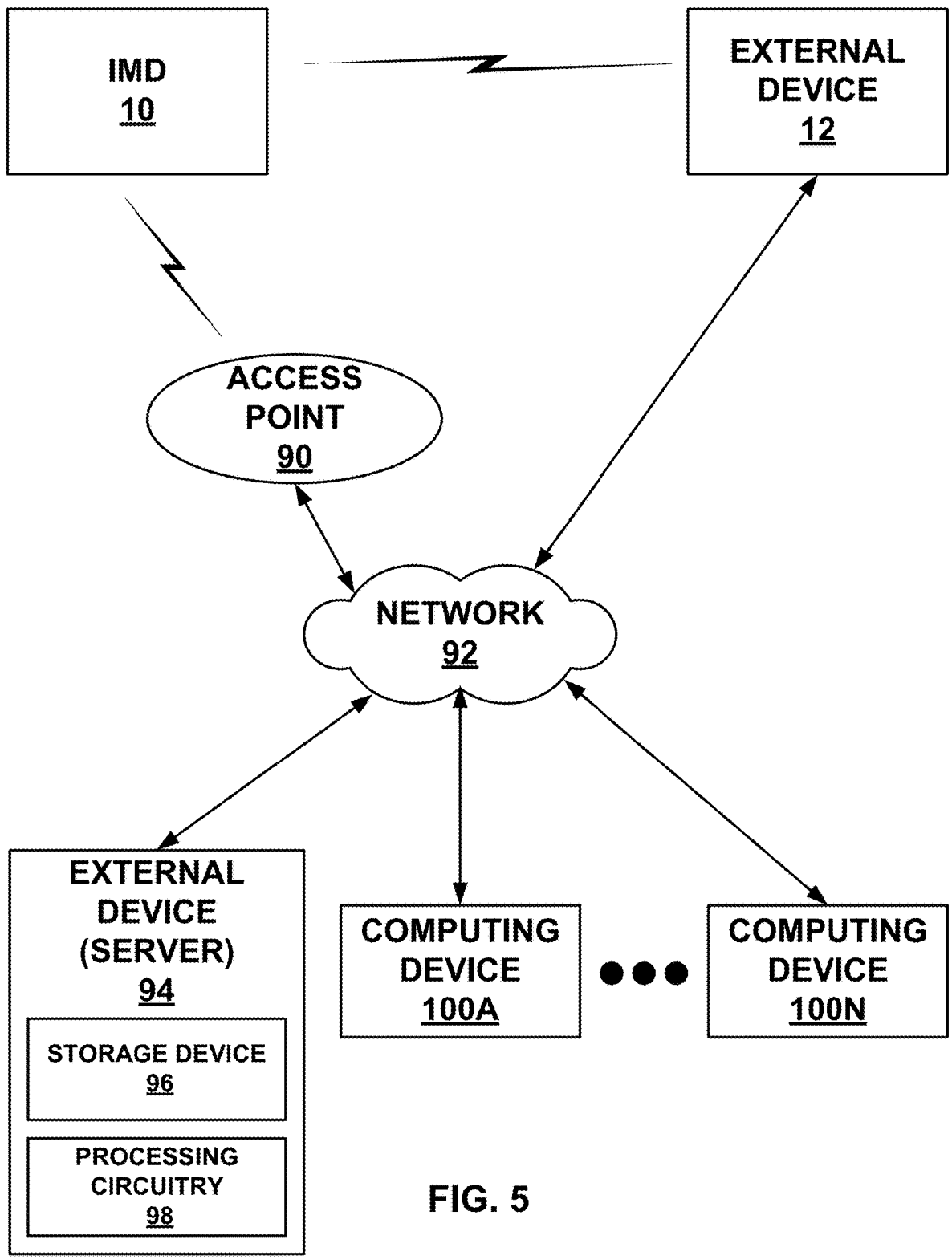
FIG. 5 is a block diagram illustrating an example system that includes an access point, a network, external computing devices, such as a server, and one or more other computing devices, which may be coupled to the IMD and external device of FIGS. 1-4.

FIG. 5 is a block diagram illustrating an example system that includes an access point 90, a network 92, external computing devices, such as a server 94, and one or more other computing devices 100A-100N (collectively, "computing devices 100"), which may be coupled to IMD 10 and external device 12 via network 92, in accordance with one or more techniques described herein. In this example, IMD 10 may use communication circuitry 54 to communicate with external device 12 via a first wireless connection, and to communicate with an access point 90 via a second wireless connection. In the example of FIG. 5, access point 90, external device 12, server 94, and computing devices 100 are interconnected and may communicate with each other through network 92.

Access point 90 may include a device that connects to network 92 via any of a variety of connections, such as telephone dial-up, digital subscriber line (DSL), or cable modem connections. In other examples, access point 90 may be coupled to network 92 through different forms of connections, including wired or wireless connections. In some examples, access point 90 may be a user device, such as a tablet or smartphone, that may be co-located with the patient. IMD 10 may be configured to transmit data, such as PVC detection information, PVC quantifications, and/or cardiac EGMs, to access point 90. Access point 90 may then communicate the retrieved data to server 94 via network 92.

In some cases, server 94 may be configured to provide a secure storage site for data that has been collected from IMD 10 and/or external device 12. In some cases, server 94 may assemble data in web pages or other documents for viewing by trained professionals, such as clinicians, via computing devices 100. One or more aspects of the illustrated system of FIG. 5 may be implemented with general network technology and functionality, which may be similar to that provided by the Medtronic CareLink® Network.

In some examples, one or more of computing devices 100 may be a tablet or other smart device located with a clinician, by which the clinician may program, receive alerts from, and/or interrogate IMD 10. For example, the clinician may access data collected by IMD 10 through a computing device 100, such as when patient 4 is in in between clinician visits, to check on a status of a medical condition. In some examples, the clinician may enter instructions for a medical intervention for patient 4 into an application executed by computing device 100, such as based on a status of a patient condition determined by IMD 10, external device 12, server 94. or any combination thereof, or based on other patient data known to the clinician. Device 100 then may transmit the instructions for medical intervention to another of computing devices 100 located with patient 4 or a caregiver of patient 4. For example, such instructions for medical intervention may include an instruction to change a drug dosage, timing, or selection, to schedule a visit with the clinician, or to seek medical attention. In further examples, a computing device 100 may generate an alert to patient 4 based on a status of a medical condition of patient 4, which may enable patient 4 proactively to seek medical attention prior to receiving instructions for a medical intervention. In this manner, patient 4 may be empowered to take action, as needed, to address his or her medical status, which may help improve clinical outcomes for patient 4.

In the example illustrated by FIG. 5, server 94 includes a storage device 96, e.g., to store data retrieved from IMD 10, and processing circuitry 98. Although not illustrated in FIG. 5 computing devices 100 may similarly include a storage device and processing circuitry. Processing circuitry 98 may include one or more processors that are configured to implement functionality and/or process instructions for execution within server 94. For example, processing circuitry 98 may be capable of processing instructions stored in memory 96. Processing circuitry 98 may include, for example, microprocessors, DSPs, ASICs, FPGAs, or equivalent discrete or integrated logic circuitry, or a combination of any of the foregoing devices or circuitry. Accordingly, processing circuitry 98 may include any suitable structure, whether in hardware, software, firmware, or any combination thereof, to perform the functions ascribed herein to processing circuitry 98. Processing circuitry 98 of server 94 and/or the processing circuitry of computing devices 100 may implement any of the techniques described herein to analyze cardiac EGMs received from IMD 10, e.g., to determine whether ventricular depolarizations are PVCs.

Storage device 96 may include a computer-readable storage medium or computer-readable storage device. In some examples, memory 96 includes one or more of a short-term memory or a long-term memory. Storage device 96 may include, for example, RAM, DRAM, SRAM, magnetic discs, optical discs, flash memories, or forms of EPROM or EEPROM. In some examples, storage device 96 is used to store data indicative of instructions for execution by processing circuitry 98.

Figure 6:
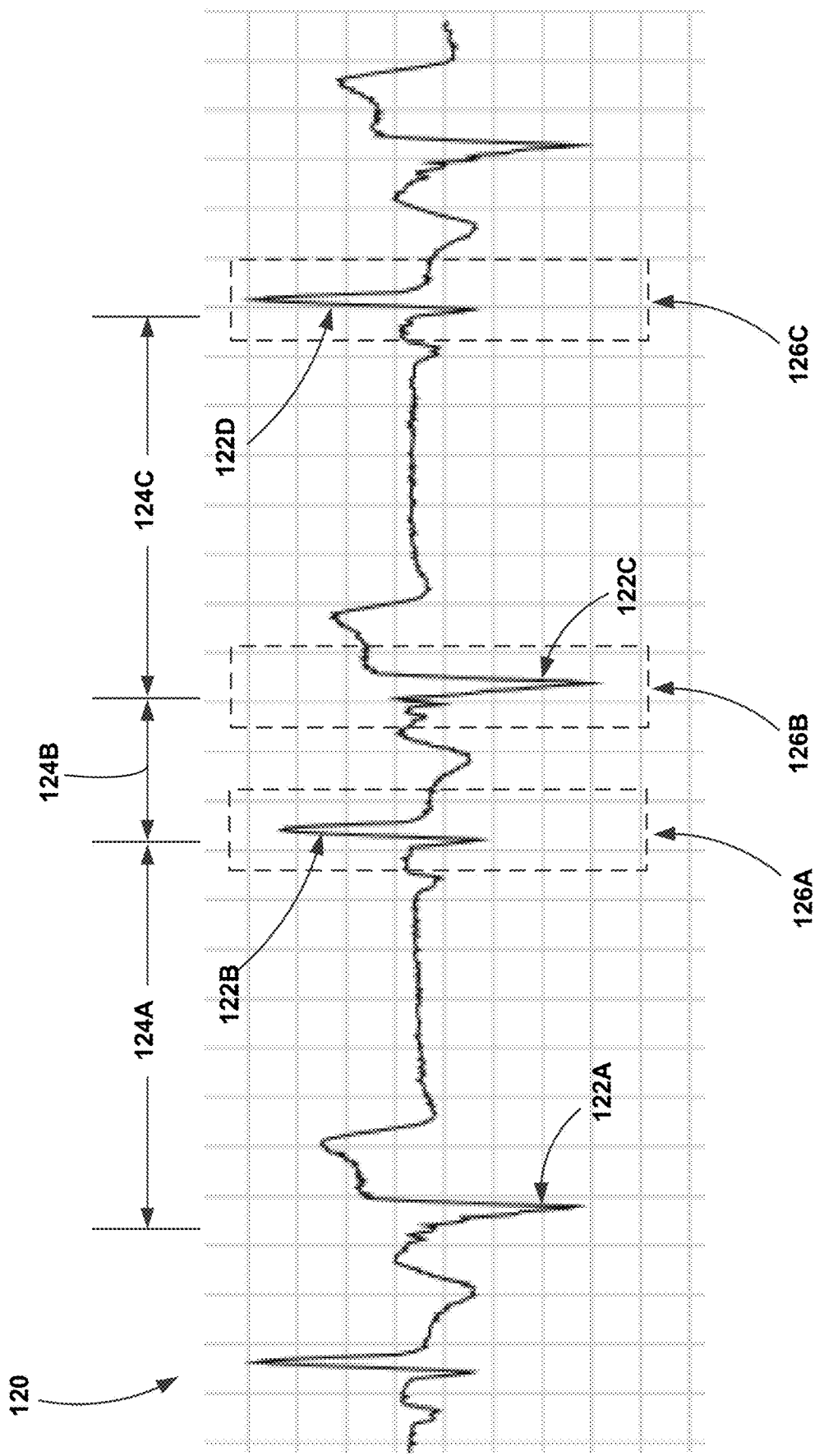
FIG. 6 is a graph illustrating a cardiac EGM including PVC depolarizations and an example technique for detecting PVC depolarizations based on the cardiac EGM.

FIG. 6 is a graph illustrating a cardiac EGM 120 including PVC depolarizations and an example technique for detecting PVC depolarizations based on cardiac EGM 120. The techniques of this disclosure use different features such as inter-depolarization (e.g., R-R) interval and morphology characteristics to distinguish a PVC depolarization from a normal ventricular depolarization. IMD 10 senses cardiac EGM 120 and detects the timing of ventricular depolarizations 122A, 122B, 122C, and 122D (collectively, "ventricular depolarizations 122") using ventricular depolarization, e.g., R-wave, detection techniques such as those described with respect to FIG. 2.

In some examples, IMD 10 senses ventricular depolarizations 122 using two or more, e.g., primary and secondary, sensing channels. The different sensing channels may have different hardware, different firmware settings, and/or different software settings for processing cardiac EGM 120 to detect ventricular depolarizations 122. For example, a primary sensing channel may implement a relatively shorter blanking, e.g., 150 milliseconds (ms), auto-adjusting threshold having relatively higher amplitudes for depolarization detection. For the primary sensing channel, some examples may implement the techniques described in U.S. Pat. No. 7,027,858, by Cao et al., which is incorporated herein by reference.

However, because the ventricular depolarization wave, e.g., QRS complexes, of PVC depolarizations are typically wider and have relatively lower frequency content than normal depolarizations, the primary sensing channel may under sense PVC depolarizations. A secondary sensing channel may include a relatively longer blanking, e.g., 520 ms, fixed threshold, which may facilitate detection of PVC depolarizations that may have not been detected by the primary sensing channel. Processing circuitry 50 and/or sensing circuitry 52 may determine the fixed threshold used by the secondary sensing channel to detect a depolarization in a given cardiac cycle based on amplitudes of one or more prior ventricular depolarizations.

Characteristics that distinguish PVC depolarizations from normal ventricular depolarizations include: shorter intervals between a PVC depolarization and the preceding adjacent (in time) depolarization; longer intervals between a PVC depolarization and a subsequent adjacent depolarization; and differing depolarization and repolarization wave morphologies as between PVC depolarizations and normal ventricular depolarizations. In order to determine whether a current ventricular depolarization 122C is a PVC depolarization, processing circuitry 50 of IMD 10 or other processing circuitry of system 2 may consider interval and morphological information for current ventricular depolarization 122C, preceding (in time) adjacent depolarization 122B, and subsequent (in time) adjacent depolarization 122D. The processing circuitry may iteratively determine whether each of ventricular depolarizations 122 is a PVC depolarization in this manner by proceeding to the next depolarization, e.g., depolarization 122C becomes the preceding adjacent depolarization, depolarization 122D becomes the current depolarization, and the next (in time) depolarization after depolarization 122D becomes the subsequent adjacent depolarization. Although the techniques for determining whether a ventricular depolarization is a PVC depolarization are described herein primarily (e.g., with respect to FIGS. 6-10) as being performed by processing circuitry 50 of IMD 10, such techniques may be performed, in whole or part, by processing circuitry of any one or more devices of system 2, such as processing circuitry 80 of external device 12, processing circuitry 98 of server 94, or processing circuitry of one or more computing devices 100.

In some examples, processing circuitry 50 determines respective inter-depolarization intervals 124A-124C (collectively "inter-depolarization intervals 124"), e.g., R-R intervals, for each of depolarizations 122. For example, processing circuitry 50 may determine inter-depolarization interval 124A for preceding adjacent depolarization 122B as the interval between the time of detection of ventricular depolarization 122A and the time of detection of ventricular depolarization 122B. Similarly, processing circuitry 50 may determine inter-depolarization interval 124B for current depolarization 122C as the interval between the time of detection of ventricular depolarization 122B and the time of detection of ventricular depolarization 122C, and inter-depolarization interval 124C for subsequent adjacent depolarization 122D as the interval between the time of detection of ventricular depolarization 122C and the time of detection of ventricular depolarization 122D.

Processing circuitry 50 may also identify respective segments of a digitized version of cardiac EGM 120 for each of ventricular depolarizations 122B-122D within respective windows 126A-126C (collectively "windows 126"). Each of windows 126 may include a predetermined number of samples, e.g., sixteen samples sampled at 64 Hz, of cardiac EGM 120. The locations of the windows 126 and, thus, which samples of cardiac EGM 120 are within a given window 126, may be set relative to the time point at which processing circuitry 50 detected the corresponding ventricular depolarization 122, or another fiducial marker of cardiac EGM 120. In some examples, each of windows 126 includes sixteen samples of cardiac EGM 120 starting four samples before the point of detection of the respective depolarization 122.

To determine whether current ventricular depolarization 122C is a PVC depolarization, processing circuitry 50 may determine whether ventricular depolarizations 122B-122D satisfy one or more morphological criteria based on the segments within respective windows 126. For each of depolarizations 122B-122D, processing circuitry 50 may determine, as examples, one or more of a maximum amplitude, a minimum amplitude, a maximum slope, and a minimum slope within the respective window 126A-126C.

Processing circuitry 50 may determine the time interval, e.g., number of samples, also referred to herein as the slope interval, between the point of the maximum slope and the point of the minimum slope for each of depolarizations 122B-122D. Processing circuitry 50 may determine the slope of cardiac EGM 120 using any known techniques, such as by determining a derivative or differential signal of cardiac EGM 120.

The morphological criteria may include criteria relating the degree of correlation between the various possible pairings of depolarizations 122B-122D. Processing circuitry 50 may determine correlation values for a pair of depolarizations by performing a correlation operation with the segments of cardiac EGM 120 within the respective windows 126 for the depolarizations. Example correlation operations include any known cross-correlation, wavelet-based comparison, feature set comparison, or difference sum techniques.

An example formula for computing cross correlation is:

$$C_{xy}(L) = \frac{1}{\text{Norm}} \sum_{k=0}^{N-|L|-1} (x_{k+|L|} - \tilde{x})(y_k - \tilde{y}) \qquad \text{Equation 1}$$

where x and y are the two segments of cardiac EGM 120 to be compared and different values of L are the different lags over which the cross-correlation is computed. This equation represents shifting one of the segments by a lag (L), multiplying it with the other segment point-by-point, and adding the multiplied result point-by-point. The same process is followed for different lags. In some examples, the lags are +/−four samples. The maximum of C(L) will happen at the lag where the two segments x and y match the best with each other. In such examples, processing circuitry 50 may determine the maximum of C(L) as the correlation value for a given comparison between two ventricular depolarizations 122.

In order to conserve the processing and power resources of IMD 10, processing circuitry 50 may implement a difference sum technique for determining correlation values representative of the degree of correlation between the various pairings of depolarizations 122B-122D. Processing circuitry 50 may determine a point-by-point difference between the segments of cardiac EGM 120 for the two depolarizations 122 at various lags, such as +/−four samples, and the lag which has the lowest difference sum will have the highest correlation between the depolarizations 122. An example formula for computing the difference sum is:

$$D_{XY}(L) = \sum_{k=0}^{N-|L|-1} x_{k+|L|} - y_k \qquad \text{Equation 2}$$

where x and y are the two segments of cardiac EGM 120 to be compared and different values of L are the different lags over which the difference sum is computed. In contrast to C(L), the lowest difference sum value D(L) will occur at the lag where the two segments x and y match best with each other. In other words, the lag with the greatest degree correlation between segments x and y will have the lowest difference sum value D(L).

In some examples, to determine whether current ventricular depolarization 122C is a PVC depolarization, processing circuitry 50 determines a correlation value between current ventricular depolarization 122C and each of preceding adjacent ventricular depolarization 122B and subsequent adjacent depolarization 122D. In the example illustrated by FIG. 6, current ventricular depolarization 122C is a PVC depolarization and both adjacent ventricular depolarizations 122B and 122D are normal ventricular depolarizations. Since ventricular depolarization 122C has a different morphology than both of adjacent ventricular depolarizations 122B and 122D, the correlation values determined by processing circuitry 50 for these two comparisons are both expected to indicate a relatively low degree of correlation, e.g., a relatively high difference sum value. Processing circuitry 50 may also determine a correlation value between adjacent ventricular depolarizations 122B and 122D. Since ventricular depolarizations 122B and 122D are both normal ventricular depolarizations expected to have similar morphologies, the correlation value between them is expected to indicate a relative high degree of correlation, e.g., a relatively low difference sum value. Processing circuitry 50 may apply any combination of one or more of the morphological criteria described herein.

To determine whether current ventricular depolarization 122C is a PVC depolarization, processing circuitry 50 may also evaluate the respective inter-depolarization intervals 124A-124C for ventricular depolarizations 122B-122D. Since current ventricular depolarization 122C is a PVC depolarization, inter-depolarization interval 124B is expected to be shorter than inter-depolarization interval 124A and inter-depolarization interval 124C is expected to be longer than inter-depolarization interval 124A due to a compensatory pause following the PVC depolarization. Processing circuitry 50 may also evaluate the maximum and minimum amplitudes, and the slope intervals, for ventricular depolarizations 122B-122D to determine whether depolarization 122C is a PVC depolarization. Since depolarization 122C is a PVC depolarization and is expected to have a wide QRS complex, the interval, e.g., number of samples, between the maximum and minimum slope for depolarization 122C is expected to be more than that of a normal depolarization, such as adjacent depolarizations 122B and 122D.

Figure 7:
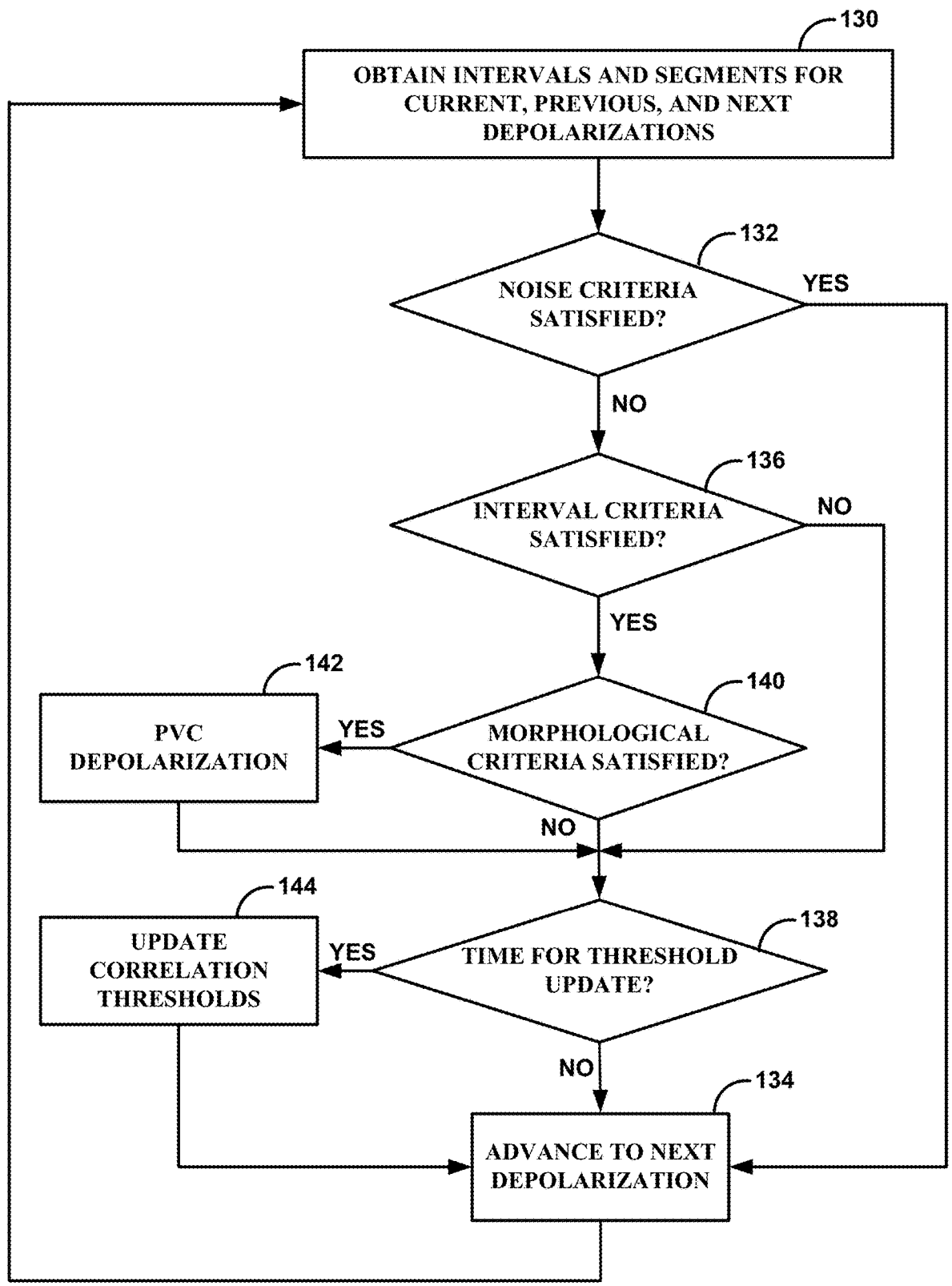
FIG. 7 is a flow diagram illustrating an example operation for detecting PVC depolarizations.

FIG. 7 is a flow diagram illustrating an example operation for detecting PVC depolarizations. Although the example operation of FIG. 7 is described as being performed by processing circuitry 50 of IMD 10 and with respect to cardiac EGM 120 of FIG. 6, in other examples some or all of the example operation may be performed by processing circuitry of another device and with respect to any cardiac EGM.

According to the example of FIG. 7, processing circuitry 50 obtains inter-depolarization intervals 124A-124C and segments of cardiac EGM 120 within windows 126A-126C for preceding adjacent ventricular depolarization 122B, current ventricular depolarization 122C, and subsequent adjacent ventricular depolarization 122D (130). Although described in the context of examples in which the two adjacent depolarizations 122B and 122D are used to determine whether depolarization 122C is a PVC depolarization, the techniques of this disclosure may be used in examples with a single adjacent depolarization, or additional depolarizations proximate in time to the current depolarization.

Processing circuitry 50 further determines whether one or more noise criteria are satisfied (132). The noise criteria may be satisfied based on the presence of one or more characteristics indicative of noise in inter-depolarization intervals 124A-124C and segments of cardiac EGM 120 within windows 126A-126C. For example, one noise criterion may be satisfied if any of inter-depolarization intervals 124A-124C is less than or equal to a short interval threshold, such as 300 ms. Another noise criterion may be satisfied if any of inter-depolarization intervals 124A-124C is greater than or equal to a long interval threshold, such as 2000 ms. Another noise criterion may be satisfied if an amplitude of any of depolarizations 122B-122D, e.g., an absolute difference between the maximum amplitude and the minimum amplitude for the depolarization, is less than or equal to a threshold, such as 25 millivolts (mV). Another noise criterion may be satisfied based on identification of a threshold number of sign changes in a first differential of any of the segments of cardiac EGM 120 within windows 126A-126C, such sign changes occurring at a sample when an absolute amplitude of the second differential of the segment is greater than or equal to a threshold.

In some examples, processing circuitry 50 may determine that the noise criteria are satisfied (YES of 132) based on any one of these criteria being satisfied for any of ventricular depolarizations 122B-122D. In some examples, processing circuitry 50 may determine that the noise criteria are satisfied (YES of 132) based on certain combinations of these criteria being satisfied. Based on determining that the noise criteria are satisfied (YES of 132), processing circuitry 50 may advance to the next depolarization 122 to determine whether that depolarization, as the current depolarization, is a PVC depolarization (134). In some examples, based on determining that the noise criteria are satisfied (YES of 132), processing circuitry 50 may advance a predetermined number of depolarizations to avoid using a noisy ventricular depolarization 122 as a current or adjacent depolarization.

Based on determining that the noise criteria are not satisfied (NO of 132), processing circuitry 50 determines whether inter-depolarization intervals 124A-124C satisfy one or more inter-depolarization interval criteria (136). In some examples, the inter-depolarization interval criteria are satisfied based on inter-depolarization intervals 124A-124C satisfying respective thresholds. The satisfaction of such respective thresholds indicates that the respective lengths of inter-depolarization intervals 124A-124C conform to what would be expected if ventricular depolarization 122C is a PVC depolarization, e.g., with interval 124B being relatively short and interval 124C being relatively long. Example inter-depolarization interval criteria are described below with respect to FIG. 8.

Based on determining that the inter-depolarization interval criteria are not satisfied (NO of 136), processing circuitry 50 may determine whether it is time to update one or more thresholds used for morphological criteria (138) and, ultimately, advance to the next ventricular depolarization 122 without indicating that the current ventricular depolarization 122C is a PVC depolarization (134). Based on determining that the inter-depolarization interval criteria are satisfied (YES of 136), processing circuitry 50 may determine whether one or more morphological criteria are satisfied (140). Processing circuitry 50 may determine whether ventricular depolarizations 122B-122D satisfy the morphological criteria based on, examples, the maximum amplitudes, minimum amplitudes, and/or slope intervals of the depolarizations, and the correlation values (e.g., cross-correlation and/or difference sum values) between the depolarizations. Example morphological criteria are described below with respect to FIG. 8.

Based on determining that the one or more morphological criteria are satisfied (YES of 140), processing circuitry 50 may determine that current ventricular depolarization 122C is a PVC depolarization (142). In this manner, the example operation of FIG. 7 requires that both inter-depolarization interval and morphological criteria are satisfied for a determination that the current ventricular depolarization is a PVC depolarization, which may facilitate a desired specificity of PVC detection. Other examples according to the techniques of this disclosure may require satisfaction of fewer, additional, or different criteria.

Whether the one or more morphological criteria are satisfied (YES of 140) or are not satisfied (NO of 140), processing circuitry 50 may determine whether it is time to update one or more thresholds used for the morphological criteria (138). For example, processing circuitry 50 may update thresholds to which correlation values of ventricular depolarizations 122B-122D are compared based on correlation values determined for previous depolarizations. In some examples, processing circuitry 50 periodically updates the thresholds based on correlation values determined during an update period, e.g., every N beats processing circuitry 50 updates the thresholds to be used for the subsequent N beats based on the correlation values determined during the N beats. N is an integer number of beats, such as twelve. Processing circuitry 50 updates the correlation thresholds (144) based on determining that it is time for a correlation threshold update (YES of 138). Example techniques for determining whether it is time for a threshold update (138) and for updating the thresholds (144) are described in further detail with respect to FIGS. 10 and 11. Whether the thresholds are updated (144) or not updated (NO 138), processing circuitry 50 may advance to the next depolarization (134) and again obtain inter depolarization intervals 124 and segments of cardiac EGM 120 within windows 126 for the new preceding adjacent ventricular depolarization, current ventricular depolarization, and subsequent adjacent ventricular depolarization to determine whether the current ventricular depolarization is a PVC depolarization (130).

As described above, processing circuitry, such as processing circuitry 50 of IMD 10, may include any combination of one or more of hardware, firmware, and software configured to implement the techniques described herein. In some examples, implementation of certain aspects of the described techniques in hardware may improve the computation and power performance of the implementing device, e.g., IMD 10. As examples, processing circuitry may include hardware configured to compute difference sums or other correlation values, maximum and minimum R-wave amplitudes, maximum and minimum slopes, slope intervals, and differential signals for identifying noise characteristics, and include firmware for other functionality described herein.

Figure 8:
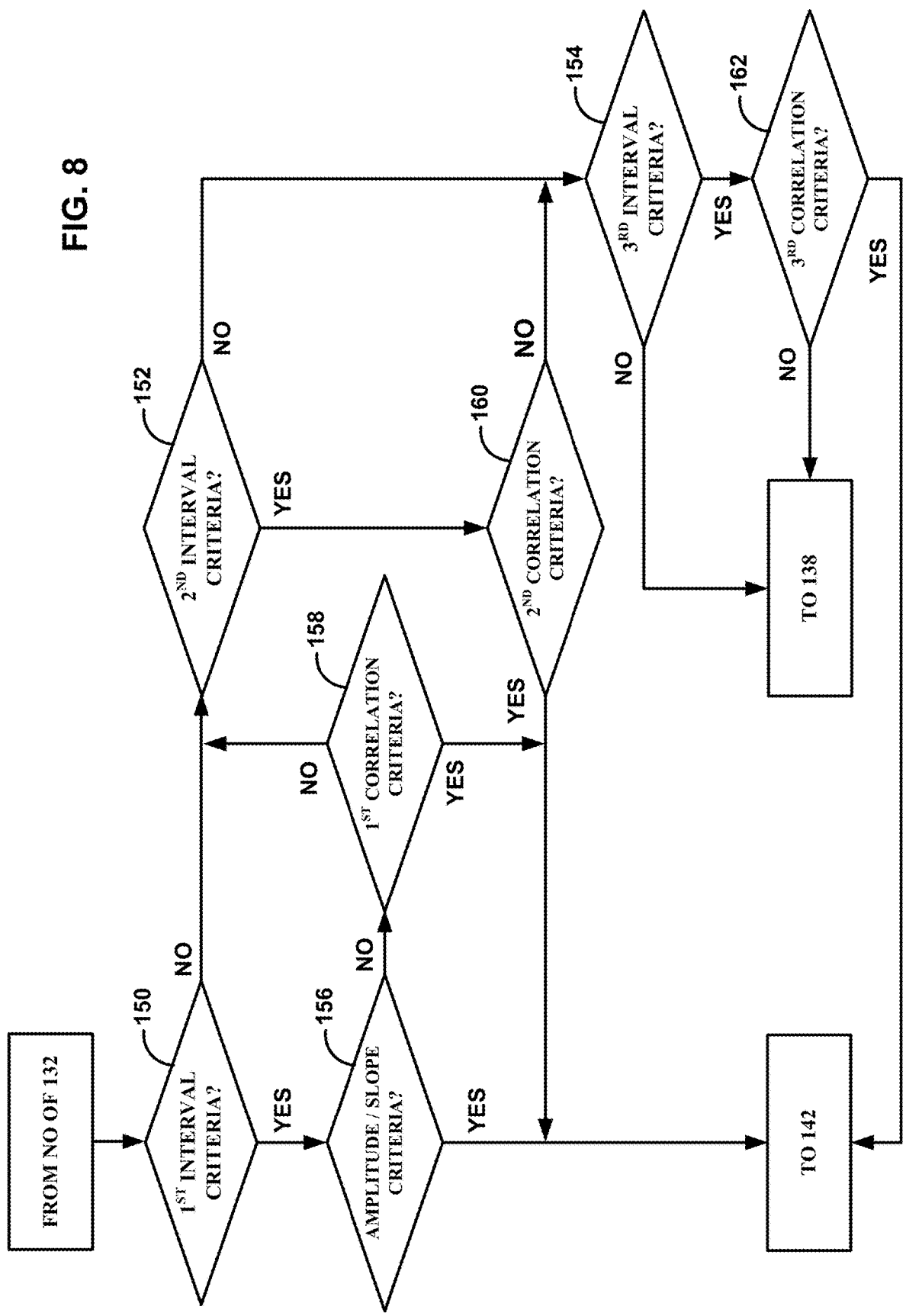
FIG. 8 is a flow diagram illustrating an example operation for determining whether interval and morphological criteria are satisfied for determining whether a current ventricular depolarization is a PVC depolarization.

FIG. 8 is a flow diagram illustrating an example operation for determining whether interval and morphological criteria are satisfied for determining whether a current ventricular depolarization is a PVC depolarization. The example operation of FIG. 8 may be an example implementation of elements 136 and 140 of FIG. 7, and is illustrated as beginning based on the noise criteria of FIG. 7 not being satisfied (NO of 132). In other examples, the example operation of FIG. 8 may be performed as part of another method for identification of PVCs.

The example operation of FIG. 8 includes various paths, each including respective, different combinations of interval and morphological criteria, based upon the satisfaction of which processing circuitry 50 may identify current ventricular depolarization 122C as a PVC depolarization (142). The combination of interval and morphological criteria may be configured to provide a desired degree of sensitivity and specificity of PVC detection.

According to the example of FIG. 8, processing circuitry 50 determines whether first inter-depolarization interval criteria are satisfied (150). If the first inter-depolarization interval criteria are not satisfied (NO of 150), then processing circuitry 50 determines whether second inter-depolarization interval criteria are satisfied (152). If the second inter-depolarization interval criteria are not satisfied (NO of 152), then processing circuitry 50 determines whether third inter-depolarization interval criteria are satisfied (154). If the third inter-depolarization interval criteria are not satisfied (NO of 154), then processing circuitry 50 does not identify current ventricular depolarization 122C as a PVC depolarization, and may proceed to determine whether it is time to update correlation thresholds (138 of FIG. 7).

In some examples, the first inter-depolarization interval criteria are that inter depolarization interval 124B is less than (inter-depolarization interval 124A-j) and less than (inter-depolarization interval 124C-j), where j is a predetermined offset, such as 10 ms. In some examples, the second inter-depolarization interval criteria are that the ratio of inter depolarization interval 124B to inter depolarization interval 124A and the ratio of inter depolarization interval 124B to inter depolarization interval 124C are both less than a predetermined ratio threshold, such as 1.25, and that inter depolarization interval 124B is less than a first predetermined inter depolarization interval threshold, such as 800 ms. In some examples, the third inter depolarization interval criteria are that inter depolarization interval 124B is less than a second predetermined inter depolarization interval threshold, such as 430 ms, and that inter depolarization interval 124A and inter depolarization interval 124C are both greater than a third predetermined inter depolarization interval threshold, such as 500 ms.

Based on determining that the first interval criteria are satisfied (YES of 150), processing circuitry 50 determines whether amplitude and/or slope criteria, which are examples of morphological criteria, are satisfied (156). Processing circuitry 50 may determine whether the amplitude and/or slope criteria are satisfied for ventricular depolarization 122C based on the maximum amplitudes, minimum amplitudes, maximum slopes, minimum slopes, and slope intervals determined for ventricular depolarizations 122B-122D in the described above with respect to FIG. 6, and as will be described further with respect to FIG. 9. Based on determining that the amplitude and/or slope criteria are satisfied (YES of 156), processing circuitry 50 may determine that current ventricular depolarization 122C is a PVC depolarization (142 of FIG. 7).

Based on determining that the amplitude and/or slope criteria are not satisfied (NO of 156), processing circuitry 50 may determine whether first correlation criteria are satisfied (158). In order to determine whether correlation criteria are satisfied, processing circuitry 50 may determine a correlation values between each pairing of ventricular depolarizations 122B-122D. In an example in which the correlation values are difference sum values determined by processing circuitry 50 as described above with respect to FIG. 6, processing circuitry 50 may determine a correlation value between ventricular depolarization 122B and ventricular depolarization 122C ($D_{n-1,n}$), a correlation value between ventricular depolarization 122C and ventricular depolarization 122D ($D_{n,n+1}$), and a correlation value between ventricular depolarization 122B and ventricular depolarization 122D ($D_{n-1,n+1}$).

In some examples, the first correlation criteria are:

$$\{D_{n-1,n+1}<(240+aThr) \text{ AND } (D_{n-1,n}-D_{n-1,n+1})>\\(100+aThr) \text{ AND } (D_{n,n+1}-D_{n-1,n+1})>(100+\\aThr)\} \text{ OR } \{D_{n-1,n+1}<(285+aThr) \text{ AND}\\(D_{n-1,n}-D_{n-1,n+1})>(165+aThr) \text{ AND } (D_{n,n+1}-\\D_{n-1,n+1})>(165+aThr)\} \quad \text{Equation 3}$$

Figure 10:
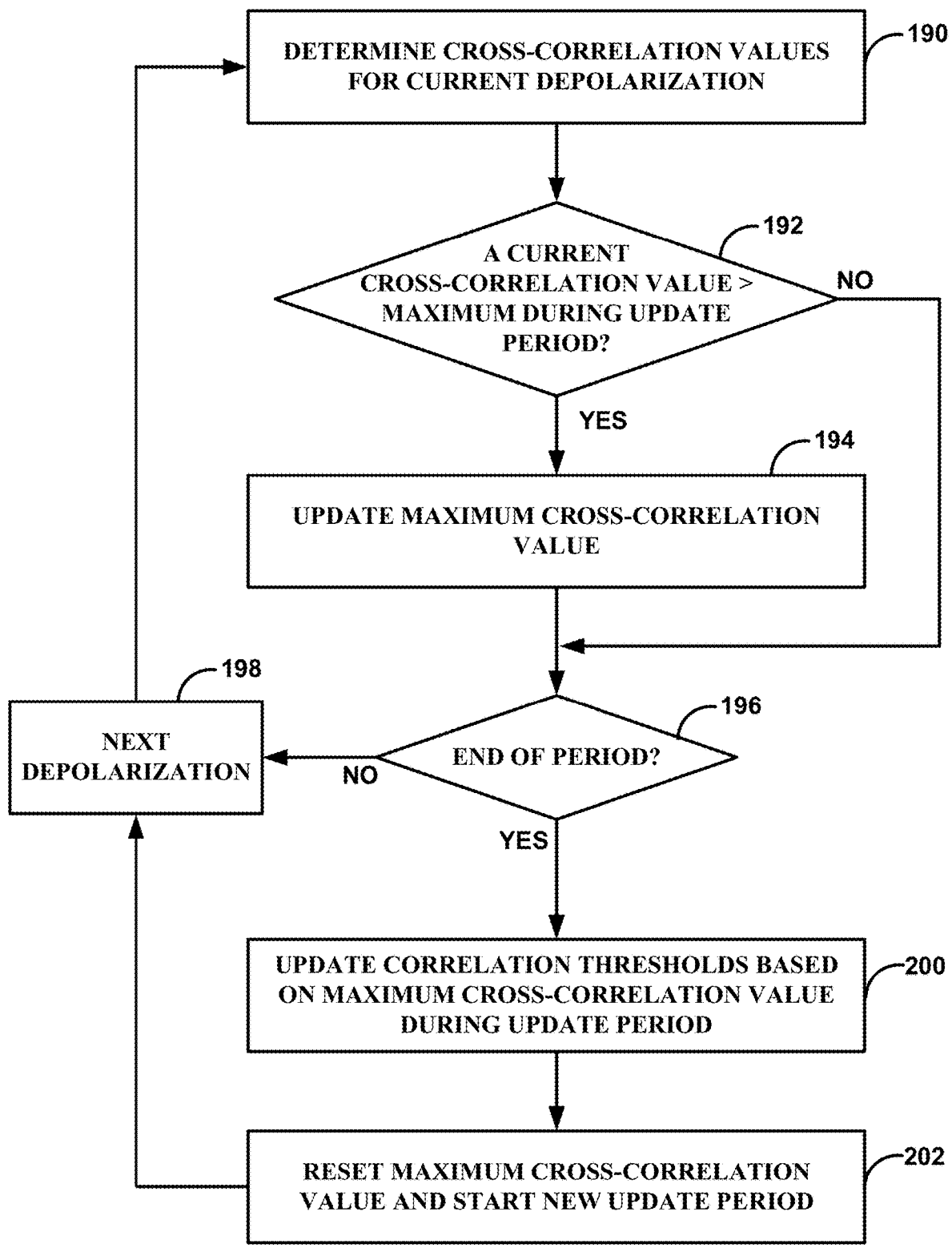
FIG. 10 is a flow diagram illustrating an example operation for adjusting correlation thresholds used for determining whether ventricular depolarizations are PVC depolarizations.
Figure 11:
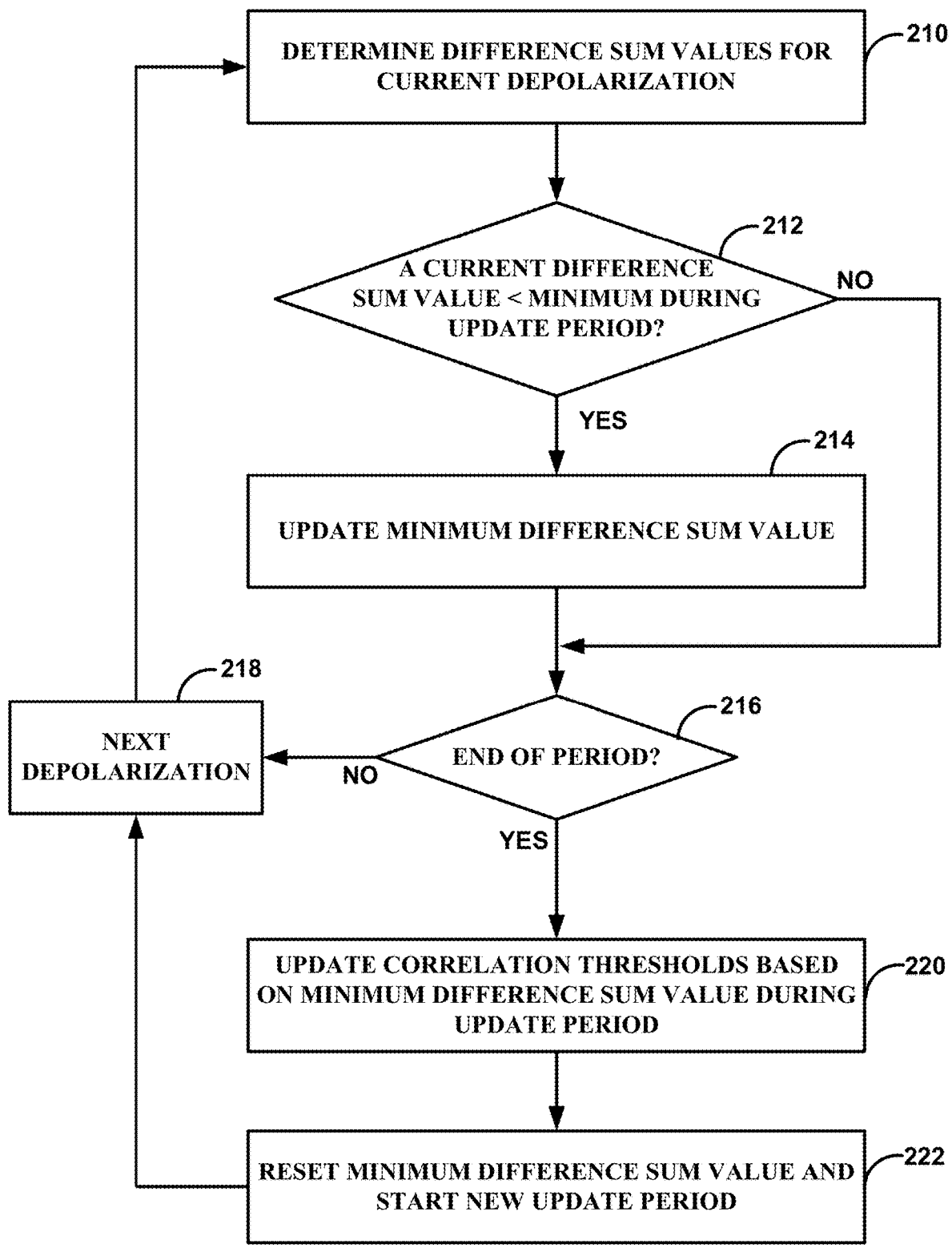
FIG. 11 is a flow diagram illustrating another example operation for adjusting correlation thresholds used for determining whether ventricular depolarizations are PVC depolarizations.

The variable aThr is an adaptive threshold value, e.g., as discussed in further detail with respect to FIGS. 10 and 11. The various constant values summed with aThr in Equations 3-5 are examples, may vary in some examples, and may be programmable in some examples.

Based on the first correlation criteria being satisfied (YES of 158), processing circuitry 50 may determine that current ventricular depolarization 122C is a PVC depolarization (142 of FIG. 7). Based on the first correlation criteria not being satisfied (NO of 158), processing circuitry 50 may determine whether the second interval criteria are satisfied (152). Based on the second interval criteria being satisfied (YES of 152), processing circuitry 50 may determine whether second correlation criteria are satisfied (160). In some examples, the second correlation criteria are:

$$\{D_{n-1,n+1}<(60+aThr) \text{ AND } (D_{n-1,n})>(180+aThr)\\\text{AND } (D_{n,n+1})>(180+aThr)\} \text{ OR } \{D_{n-1,n+1}<\\(130+aThr) \text{ AND } (D_{n-1,n})>(250+aThr) \text{ AND}\\(D_{n,n+1})>(250+aThr)\} \quad \text{Equation 4}$$

Based on the second correlation criteria being satisfied (YES of 160), processing circuitry 50 may determine that current ventricular depolarization 122C is a PVC depolarization (142 of FIG. 7). Based on the second correlation criteria not being satisfied (NO of 160), processing circuitry 50 may determine whether the third interval criteria are satisfied (154). Based on the third interval criteria being satisfied (YES of 154), processing circuitry 50 may determine whether third correlation criteria are satisfied (162). In some examples, the third correlation criteria are:

$$D_{n-1,n+1}<(245+aThr) \text{ AND } (D_{n-1,n}-D_{n-1,n+1})>\\(35+aThr) \text{ AND } (D_{n,n+1}-D_{n-1,n+1})>(35+aThr) \quad \text{Equation 5}$$

Based on the third correlation criteria being satisfied (YES of 162), processing circuitry 50 may determine that current ventricular depolarization 122C is a PVC depolarization (142 of FIG. 7). Based on the third correlation criteria not being satisfied (NO of 162), processing circuitry 50 does not identify current ventricular depolarization 122C as a PVC depolarization, and may proceed to determine whether it is time to update correlation thresholds (138 of FIG. 7). Although the example operation of FIG. 8 includes identifying the current ventricular depolarization as a PVC depolarization (142) if one or more criteria are satisfied, and proceeding to determine whether it is time to update correlation thresholds (138) if the criteria are not satisfied, it should be understood that processing circuitry may also determine whether it is time to update correlation thresholds (138) after identifying the current ventricular depolarization as a PVC depolarization (142), as illustrated in FIG. 7.

Additionally, although FIG. 8 is described in the context of an example in which the correlation values determined between depolarizations are difference sum values, the techniques of FIG. 8 may be applied to examples in which processing circuitry 50 determines other values indicative of the degree of correlation of the morphologies of ventricular depolarizations such as cross-correlation values. As described herein a greater degree of correlation is indicated by larger cross-correlation values and smaller difference sum values. To account for this difference, in examples in which the correlation values are cross-correlation values rather than difference sum values, the morphological criteria may be modified. For example, the directionality of the comparisons (e.g., > or <) and calculation of thresholds used in Equations 3-5 may be modified in examples in which the correlation values are cross-correlation values.

Figure 9:
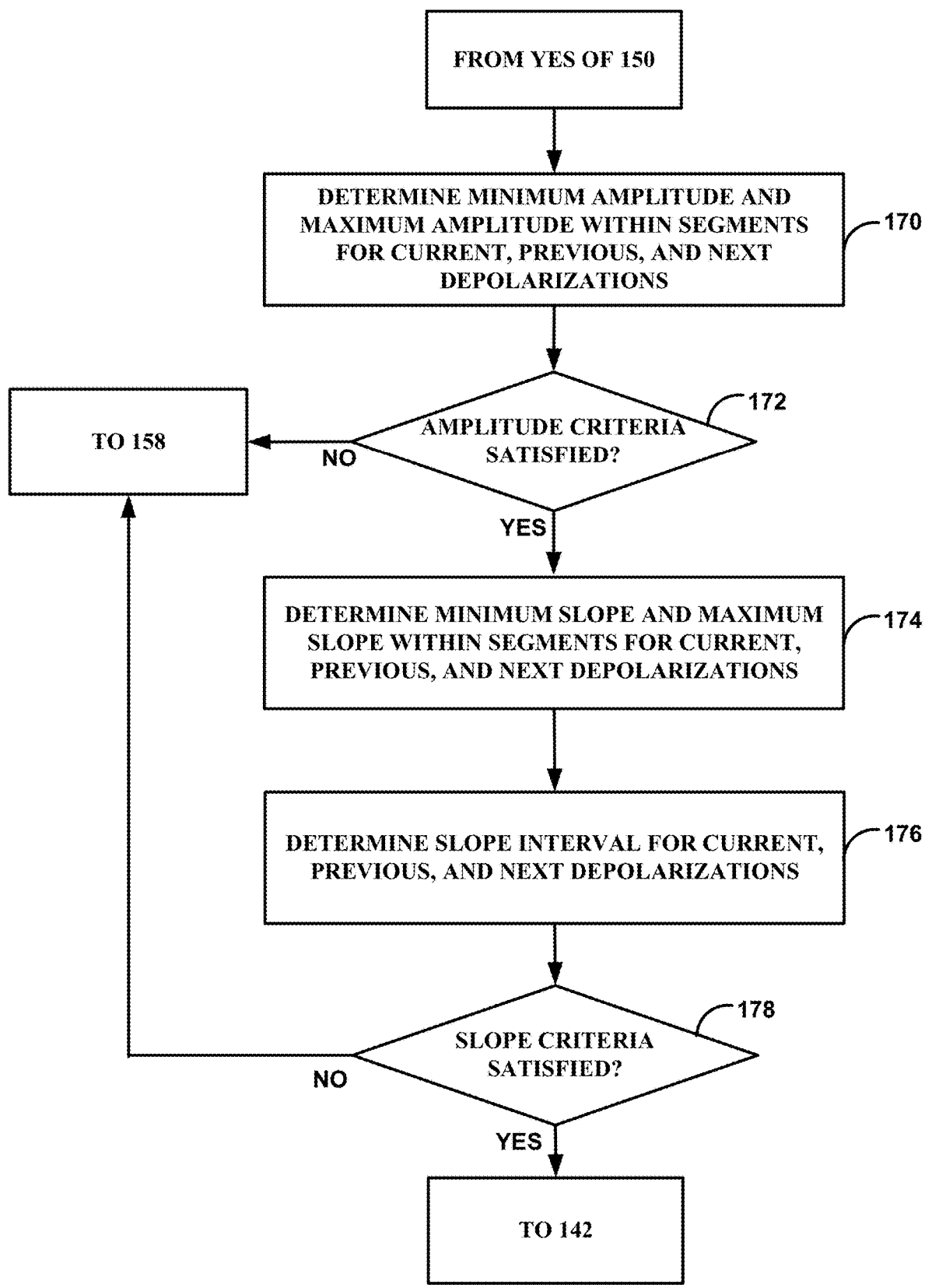
FIG. 9 is a flow diagram illustrating an example operation for determining whether amplitude and slope based morphological criteria are satisfied for determining whether a current depolarization is a PVC depolarization.

FIG. 9 is a flow diagram illustrating an example operation for determining whether amplitude and slope based morphological criteria are satisfied for determining whether a current depolarization is a PVC. The example operation of FIG. 9 may be an example implementation of element 156 of FIG. 8, and is illustrated as beginning based on the first interval criteria of FIG. 8 being satisfied (YES of 150). In other examples, the example operation of FIG. 9 may be performed as part of another method for identification of PVCs.

According to the example of FIG. 9, processing circuitry 50 determines a respective maximum amplitude ($maxR_{n-i,n,n+1}$) and respective minimum amplitude ($minR_{n-1,n,n+1}$) for each of depolarizations 122B-122D, e.g., the maximum amplitude and minimum amplitude of cardiac EGM 120 within each of windows 126A-126C (170). Processing circuitry 50 further determines whether the maximum and minimum amplitudes satisfy one or more amplitude criteria (172). In some examples, processing circuitry 50 compares the maximum amplitudes of the depolarizations to each other, the minimum amplitudes of the depolarizations to each other, and/or difference between the maximum and minimum amplitudes for each depolarization to the differences for the other depolarizations. In some examples, the amplitude criteria are:

$$MnMxD_{n-1,n+1}<60 \text{ AND } MnMxD_{n-1,n}>30 \text{ AND}\\MnMxD_{n,n+1}>30$$

where, $MnMxD_{x,y}$ is absolute ($maxR_x-maxR_y$)+absolute($minR_x-minR_y$) $\quad$ Equation 6

The various thresholds in Equation 6 are examples, may vary in some examples, and may be programmable in some examples. Based on processing circuitry 50 determining that the one or more amplitude criteria are not satisfied (NO of 172), processing circuitry 50 may determine whether first correlation criteria are satisfied (158 of FIG. 8). Based on processing circuitry 50 determining that the one or more amplitude criteria are satisfied (YES of 172), processing circuitry 50 may determine a respective maximum slope and a respective minimum slope for each of depolarizations 122B-122D, e.g., based on the maximum slope and minimum slope of cardiac EGM 120 within each of windows 126A-126C (174). Processing circuitry 50 may determine a respective slope interval, e.g., number of samples or amount of time, between the maximum slope and the minimum slope (slopeint$_{n-1,n,n+1}$) for each of depolarizations 122B-122D (176).

Processing circuitry 50 determines whether one or more of the maximum slopes, minimum slopes, or slope intervals satisfy one or more slope criteria (178). In some examples, processing circuitry 50 determines whether the one or more slope criteria are satisfied by comparing the respective slope intervals for depolarizations 122B-122D to each other to determine a comparison metric, e.g., a difference or a ratio, and determining whether the comparison metrics satisfy one or more criteria. In some examples, processing circuitry determines whether a first comparison metric for the comparison of the preceding adjacent ventricular depolarization 122B to the subsequent adjacent ventricular depolarization 122D satisfies a similarity criterion, and determines whether a second comparison metric for the comparison of the preceding adjacent ventricular depolarization 122B to the current ventricular depolarization 122C, and a third comparison metric for the comparison of the subsequent adjacent ventricular depolarization 122D to the current ventricular depolarization 122C satisfy a dissimilarity criterion. If the current ventricular depolarization is a PVC depolarization, then it would be expected that its slope interval would be longer than, and thus dissimilar to, the slope intervals of the adjacent depolarizations. In some examples, the slope criteria are:

$$SD_{n-1,n+1} < 7 \text{ AND } SD_{n-1,n} > 2 \text{ and } SD_{n,n+1} > 2,$$

where, $SD_{xy}$ is absolute(slopeint$_x$−slopeint$_y$)     Equation 7

The various thresholds in Equation 7 are examples, may vary in some examples, and may be programmable in some examples. Furthermore, rather than an absolute value of the difference, $SD_{xy}$ may equal slopeint$_x$−slopeint$_y$ in some examples. Based on processing circuitry 50 determining that the one or more slope criteria are not satisfied (NO of 178), processing circuitry 50 may determine whether first correlation criteria are satisfied (158 of FIG. 8). Based on processing circuitry 50 determining that the one or more slope criteria are satisfied (YES of 178), processing circuitry 50 may determine current ventricular depolarization 122C is a PVC depolarization (142 of FIG. 7).

FIGS. 10 and 11 are flow diagrams illustrating example operations for adjusting correlation thresholds used for determining whether ventricular depolarizations are PVC depolarizations. The operations of FIGS. 10 and 11 may generally correspond to elements 138 and 144 of FIG. 7, in some examples. Processing circuitry 50 may periodically update thresholds used to identify PVC depolarizations based on correlation values in order to compensate for variations in the amplitude and morphology of cardiac EGM 120 over time that are unrelated to whether a given ventricular depolarization is normal or the result of a PVC.

FIG. 10 illustrates an example in which the correlation values are cross-correlation values, and FIG. 11 illustrates an example in which the correlation values are difference sum values. Both of the examples of FIGS. 10 and 11 adjust the correlation thresholds based on the correlation value determined during the update period that represents the greatest degree of correlation between the morphologies of two depolarizations. However, the cross-correlation value indicating the greatest degree of correlation between the morphologies of two depolarizations is the maximum cross-correlation value, while the difference sum value indicating the greatest degree of correlation between the morphologies of two depolarizations is the minimum difference sum value.

According to the example of FIG. 10, processing circuitry 50 determines cross-correlation values for depolarizations 122B-122D, e.g., $C_{n-1,n+1}$, $C_{n-1,n}$, and $C_{n,n+1}$, for determining whether current ventricular depolarization 122C is a PVC depolarization based on whether one or more correlation criteria are satisfied (190). Processing circuitry 50 further determines whether one of the current cross-correlation values is greater than the maximum cross-correlation value previously identified during the current update period (192). In some examples, processing circuitry 50 considers less than all of the correlation values determined for a particular current ventricular depolarization, e.g., such as only $C_{n-1,n+1}$, $C_{n-1,n}$, for purposes of determining a maximum cross-correlation value during an update period.

Based on determining that a current cross-correlation value is greater than the existing maximum for the update period (YES of 192), processing circuitry 50 updates the period maximum cross-correlation value to be the current correlation value (194). Whether the maximum cross-correlation value is updated (194) or not (NO of 192), processing circuitry 50 determines whether the end of an update period has been reached (196). Based on determining that the end of the update period has not been reached (NO of 196), processing circuitry 50 may proceed to evaluation of the cross-correlation values for the next current ventricular depolarization (198). Based on determining that the end of the update period has been reached (YES of 196), processing circuitry 50 may update one or more correlation thresholds, e.g., a value of aThr, based on the maximum cross-correlation value during the update period (200). Processing circuitry 50 may further reset the maximum cross-correlation value to a predetermined update period start value, and start a new update period (202).

According to the example of FIG. 11, processing circuitry 50 determines difference sum values for depolarizations 122B-122D, e.g., $D_{n-1,n+1}$, $D_{n-1,n}$, and for determining whether current ventricular depolarization 122C is a PVC depolarization based on whether one or more correlation criteria are satisfied (210). Processing circuitry 50 further determines whether one of the current difference sum values is less than a minimum difference sum value previously identified during the current update period (212). In examples in which the correlation values are difference sum values, the maximum degree of correlation will be represented by the minimum difference sum value. In some examples, processing circuitry 50 considers less than all of the difference sum value determined for a particular current ventricular depolarization, e.g., such as only $D_{n-1,n+1}$, $D_{n-1,n}$, for purposes of determining a minimum difference sum value during an update period.

Based on determining that a current difference sum value is less than the existing minimum difference sum value for the update period (YES of 212), processing circuitry 50 updates the period minimum difference sum value to be the current difference sum value (214). Whether the minimum difference sum value is updated (214) or not (NO of 212), processing circuitry 50 determines whether the end of an update period has been reached (216). Based on determining that the end of the update period has not been reached (NO of 216), processing circuitry 50 may proceed to evaluation of the difference sum values for the next current ventricular depolarization (218). Based on determining that the end of the update period has been reached (YES of 216), processing circuitry 50 may update one or more correlation thresholds, e.g., a value of aThr, based on the minimum difference sum value during the update period (220). Processing circuitry 50 may further reset the minimum difference sum value to a predetermined update period start value, and start a new update period (222).

In some examples, processing circuitry 50 determines whether difference sum values Dn−1,n+1, Dn−1,n for determining whether current ventricular depolarization 122C is a PVC depolarization are less than the existing minimum difference sum value during an update period of N cardiac cycles, such as 12 cardiac cycles. After evaluating 2N difference sum values (e.g., 2 from each cardiac cycle where there is no noise), processing circuitry 50 may update the adaptive threshold (aThr) by the running minimum and resetting the running minimum to a predetermined update period start value, e.g., 5000. In some examples, processing circuitry 50 may update aThr according to the following:

$$\text{minCorr}=\text{minimum}\{5000;Dn-1,n+1;Dn-1,n\} \text{ for } n=1 \text{ to } 12 \qquad \text{Equation 8}$$

$$aThr=(\text{minCorr}-25)/2 \text{ with a minimum allowed value for } aThr \text{ of } -120 \text{ and a maximum of } 230 \qquad \text{Equation 9}$$

The values of 5000, 12, 25, −120, and 230 may be fixed or programmable in some examples.

The techniques described in this disclosure may be implemented, at least in part, in hardware, software, firmware, or any combination thereof. For example, various aspects of the techniques may be implemented within one or more microprocessors, DSPs, ASICs, FPGAs, or any other equivalent integrated or discrete logic QRS circuitry, as well as any combinations of such components, embodied in external devices, such as physician or patient programmers, stimulators, or other devices. The terms "processor" and "processing circuitry" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be embodied as instructions on a computer-readable storage medium such as RAM, DRAM, SRAM, magnetic discs, optical discs, flash memories, or forms of EPROM or EEPROM. The instructions may be executed to support one or more aspects of the functionality described in this disclosure.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

What is claimed is:

1. A medical system comprising:
 a plurality of electrodes configured to sense a cardiac electrogram of a patient;
 processing circuitry configured to:
  identify a plurality of ventricular depolarizations within the cardiac electrogram;
  for each of the plurality of ventricular depolarizations, identify a maximum slope point, a minimum slope point, and an interval from the maximum slope point to the minimum slope point;
  for each of the plurality ventricular depolarizations as a current ventricular depolarization:
   determine that the intervals from the maximum slope point to the minimum slope point for the current ventricular depolarization, a preceding adjacent ventricular depolarization of the plurality of ventricular depolarizations, and a subsequent adjacent ventricular depolarization of the plurality of ventricular depolarizations satisfy one or more slope criteria; and
   determine that the current ventricular depolarization is a premature ventricular contraction (PVC) depolarization based on the intervals from the maximum slope point to the minimum slope point satisfying the one or more slope criteria; and
  determine a PVC detection quantification for the patient based on the determinations that the plurality of ventricular depolarizations are PVCs; and
 communication circuitry configured to transmit data comprising the PVC detection quantification determined by the processing circuitry to a user computing device.

2. The medical system of claim 1, wherein, to determine that the intervals from the maximum slope point to the minimum slope point satisfy the one or more slope criteria, the processing circuitry is configured to:
 compare the intervals to each other;
 determine a respective comparison metric value for each of the comparisons; and
 determine whether the comparison metric values satisfy the one or more slope criteria.

3. The medical system of claim 2, wherein, to determine that the comparison metric values satisfy the one or more slope criteria, the processing circuitry is configured to:
 determine that a first comparison metric for the comparison of the preceding adjacent ventricular depolarization to the subsequent adjacent ventricular depolarization satisfies a similarity criterion; and
 determine that a second comparison metric for the comparison of the preceding adjacent ventricular depolarization to the current ventricular depolarization and a third comparison metric for the comparison of the subsequent adjacent ventricular depolarization to the current ventricular depolarization satisfy a dissimilarity criterion.

4. The medical system of claim 2, wherein the comparison metric values comprise respective differences between each of the intervals and, to determine that the comparison metric values satisfy the one or more slope criteria, the processing circuitry is configured to:
- determine that a first difference between the intervals of the preceding adjacent ventricular depolarization and the subsequent adjacent ventricular depolarization is less than a first threshold; and
- determine that a second difference between the intervals of the preceding adjacent ventricular depolarization and the current ventricular depolarization and a third difference between the intervals of the intervals of the subsequent adjacent ventricular depolarization and the current ventricular depolarization exceed a second threshold.

5. The medical system of claim 1, wherein the processing circuitry is further configured to:
- for each of the plurality of ventricular depolarizations, identify a maximum amplitude and a minimum amplitude; and
- for each of the plurality ventricular depolarizations as the current ventricular depolarization:
  - determine that the maximum amplitudes and minimum amplitudes for the current ventricular depolarization, the preceding adjacent ventricular depolarization, and the subsequent adjacent ventricular depolarization satisfy one or more amplitude criteria; and
  - determine that the current ventricular depolarization is a PVC depolarization based on the maximum amplitudes and minimum amplitudes satisfying the one or more amplitude criteria.

6. The medical system of claim 5, wherein the processing circuitry is configured to, for each pairing of one of the preceding adjacent ventricular depolarization, the current ventricular depolarization, and the subsequent adjacent ventricular depolarization with another of the preceding adjacent ventricular depolarization, the current ventricular depolarization, and the subsequent adjacent ventricular depolarization:
- compare the maximum amplitudes of the depolarizations to each other; and
- compare the minimum amplitudes of the depolarizations to each other,
- wherein, to determine that the current ventricular depolarization is a PVC depolarization, the processing circuitry is configured determine that the comparisons satisfy the one or more amplitude criteria.

7. The medical system of claim 1, wherein the processing circuitry is further configured to, for each of the plurality of ventricular depolarizations, determine an inter-depolarization interval and, for each of the plurality ventricular depolarizations as the current ventricular depolarization:
- determine that the inter-depolarization intervals of the current ventricular depolarization, the preceding adjacent ventricular depolarization, and the subsequent adjacent ventricular depolarization satisfy one or more inter-depolarization interval criteria; and
- determine that the current ventricular depolarization is a PVC depolarization based on the inter-depolarization intervals satisfying the one or more inter-depolarization interval criteria.

8. The medical system of claim 1, wherein the processing circuitry is further configured to, for each of the plurality ventricular depolarizations as the current ventricular depolarization:
- determine a correlation value between each pairing of one of the preceding adjacent ventricular depolarization, the current ventricular depolarization, and the subsequent adjacent ventricular depolarization and another of the preceding adjacent ventricular depolarization, the current ventricular depolarization, and the subsequent adjacent ventricular depolarization;
- determine that the correlation values satisfy one or more correlation criteria; and
- determine that the current ventricular depolarization is a PVC depolarization based on the correlation values satisfying the one or more correlation criteria.

9. The medical system of claim 8, wherein, to determine the correlation values, the processing circuitry is configured to determine a difference sum for each pairing of one of the preceding adjacent ventricular depolarization, the current ventricular depolarization, and the subsequent adjacent ventricular depolarization and another of the preceding adjacent ventricular depolarization, the current ventricular depolarization, and the subsequent adjacent ventricular depolarization.

10. The medical system of claim 8, wherein the one or more correlation criteria comprise one or more thresholds, and the processing circuitry is configured to:
- for a plurality of correlation values determined during an update period preceding the current depolarization, identify one of the plurality of correlation values representing a maximum amount of correlation among the plurality of correlation values; and
- adjust the one or more thresholds based on the identified one of the plurality of correlation values.

11. The medical system of claim 1, wherein, to identify the plurality of ventricular depolarizations, the processing circuitry is configured to apply a primary sensing channel and a secondary sensing channel to the cardiac electrogram, wherein the primary and secondary sensing channels have different blanking periods and amplitude thresholds.

12. The medical system of claim 1, wherein the plurality of ventricular depolarizations comprises a subset of depolarizations identified by the processing circuitry, wherein the processing circuitry is configured to exclude ventricular depolarizations from the subset based on the excluded ventricular depolarizations satisfying one or more noise criteria, wherein the one or more noise criteria include one or more of an inter-depolarization interval criterion, an amplitude criterion, and a sign change criterion.

13. A medical system comprising:
- a plurality of electrodes configured to sense a cardiac electrogram of a patient;
- processing circuitry configured to:
  - identify a plurality of ventricular depolarizations within the cardiac electrogram;
  - for each of the plurality ventricular depolarizations as a current ventricular depolarization:
    - determine a correlation value between each pairing of one of the current ventricular depolarization, a preceding adjacent ventricular depolarization, and a subsequent adjacent ventricular depolarization and another of the preceding adjacent ventricular depolarization, the current ventricular depolarization, and the subsequent adjacent ventricular depolarization;
    - determine that the correlation values satisfy one or more correlation criteria comprising one or more thresholds; and
    - determine that the current ventricular depolarization is a premature ventricular contraction (PVC) depolarization based on the correlation values satisfying the one or more correlation criteria; and determine a PVC detection quantification for the patient based on the determinations that the plurality of ventricular depolarizations are PVCs, wherein the processing circuitry is further configured to:
for a plurality of correlation values determined during an update period preceding the current depolarization, identify one of the plurality of correlation values representing a maximum degree of correlation among the plurality of correlation values; and
adjust the one or more thresholds based on the identified one of the plurality of correlation values; and
communication circuitry configured to transmit data comprising the PVC detection quantification determined by the processing circuitry to a user computing device.

14. The medical system of claim 13, wherein, to determine the correlation values, the processing circuitry is configured to determine a difference sum for each pairing of one of the preceding adjacent ventricular depolarization, the current ventricular depolarization, and the subsequent adjacent ventricular depolarization and another of the preceding adjacent ventricular depolarization, the current ventricular depolarization, and the subsequent adjacent ventricular depolarization.

15. The medical system of claim 14, wherein the identified one of the plurality of correlation values comprises a minimum difference sum determined during the update period.

16. The medical system of claim 14, wherein the processing circuitry comprises hardware configured to determine the difference sums.

17. The medical system of claim 1, further comprising sensing circuitry coupled to the plurality of electrodes, the sensing circuitry configured to provide a digitized version of the cardiac electrogram to the processing circuitry, wherein, to identify the plurality of ventricular depolarizations within the cardiac electrogram, the processing circuitry is configured to identify the plurality of ventricular depolarizations within the digitized version of the cardiac electrogram.

18. The medical system of claim 13, further comprising sensing circuitry configured to provide a digitized version of the cardiac electrogram to the processing circuitry, wherein the sensing circuitry is configured to identify the plurality of ventricular depolarizations within the cardiac electrogram by identifying the plurality of ventricular depolarizations within the digitized version of the cardiac electrogram.

19. The medical system of claim 1, further comprising an insertable cardiac monitor comprising the electrodes, the processing circuitry, and the communication circuitry.

20. The medical system of claim 13, further comprising an insertable cardiac monitor comprising the electrodes, the processing circuitry, and the communication circuitry.

21. An insertable cardiac monitor comprising:
a housing configured for subcutaneous implantation within a patient, the housing having a length, a width, and a depth, wherein the length is greater than each of the width and the depth;
a plurality of electrodes positioned at the outer surface of the housing and configured to continuously sense a cardiac electrogram of the patient while the insertable cardiac monitor is subcutaneously implanted within the patient over a period of time greater than several days;
processing circuitry and a memory coupled to the processing circuitry, the processing circuitry and the memory positioned within the housing, wherein the processing circuitry is configured to:
identify a plurality of ventricular depolarizations within the cardiac electrogram;
for each of the plurality of ventricular depolarizations, identify a maximum slope point, a minimum slope point, and an interval from the maximum slope point to the minimum slope point;
for each of the plurality ventricular depolarizations as a current ventricular depolarization:
determine that the intervals from the maximum slope point to the minimum slope point for the current ventricular depolarization, a preceding adjacent ventricular depolarization of the plurality of ventricular depolarizations, and a subsequent adjacent ventricular depolarization of the plurality of ventricular depolarizations satisfy one or more slope criteria; and
determine that the current ventricular depolarization is a premature ventricular contraction (PVC) depolarization based on the intervals from the maximum slope point to the minimum slope point satisfying the one or more slope criteria; and
determine a PVC detection quantification for the patient based on the determinations that the plurality of ventricular depolarizations are PVCs; and
communication circuitry positioned within the housing and configured to transmit data comprising the PVC detection quantification determined by the processing circuitry via a network.

22. The insertable cardiac monitor of claim 21, wherein, to determine that the intervals from the maximum slope point to the minimum slope point satisfy the one or more slope criteria, the processing circuitry is configured to:
compare the intervals to each other;
determine a respective comparison metric value for each of the comparisons; and
determine whether the comparison metric values satisfy the one or more slope criteria.

23. The insertable cardiac monitor of claim 22, wherein, to determine that the comparison metric values satisfy the one or more slope criteria, the processing circuitry is configured to:
determine that a first comparison metric for the comparison of the preceding adjacent ventricular depolarization to the subsequent adjacent ventricular depolarization satisfies a similarity criterion; and
determine that a second comparison metric for the comparison of the preceding adjacent ventricular depolarization to the current ventricular depolarization and a third comparison metric for the comparison of the subsequent adjacent ventricular depolarization to the current ventricular depolarization satisfy a dissimilarity criterion.

24. The insertable cardiac monitor of claim 21, further comprising sensing circuitry within the housing and coupled to the plurality of electrodes, the sensing circuitry configured to provide a digitized version of the cardiac electrogram to the processing circuitry, wherein the processing circuitry is further configured to determine a respective window having a predetermined number of samples of the digitized version of the cardiac electrogram for each of the plurality of depolarizations, and for each of the plurality ventricular depolarizations as the current ventricular depolarization:
determine a correlation value between the samples of the windows for each pairing of one of the preceding adjacent ventricular depolarization, the current ventricular depolarization, and the subsequent adjacent ventricular depolarization and another of the preceding adjacent ventricular depolarization, the current ventricular depolarization, and the subsequent adjacent ventricular depolarization;
determine that the correlation values satisfy one or more correlation criteria; and
determine that the current ventricular depolarization is a PVC depolarization based on the correlation values satisfying the one or more correlation criteria.

25. The insertable cardiac monitor of claim 24, wherein, to determine the each correlation values, the processing circuitry is configured to determine a difference sum of the samples of the windows.

26. A medical system comprising:
an insertable cardiac monitor comprising:
a housing configured for subcutaneous implantation within a patient, the housing having a length, a width, and a depth, wherein the length is greater than each of the width and the depth;
a plurality of electrodes positioned at the outer surface of the housing and configured to continuously sense a cardiac electrogram of the patient while the insertable cardiac monitor is subcutaneously implanted within the patient over a period of time greater than several days;
processing circuitry and a memory coupled to the processing circuitry, the processing circuitry and the memory positioned within the housing, wherein the processing circuitry is configured to:
identify a plurality of ventricular depolarizations within the cardiac electrogram;
for each of the plurality of ventricular depolarizations, identify a maximum slope point, a minimum slope point, and an interval from the maximum slope point to the minimum slope point;
for each of the plurality ventricular depolarizations as a current ventricular depolarization:
determine that the intervals from the maximum slope point to the minimum slope point for the current ventricular depolarization, a preceding adjacent ventricular depolarization of the plurality of ventricular depolarizations, and a subsequent adjacent ventricular depolarization of the plurality of ventricular depolarizations satisfy one or more slope criteria; and
determine that the current ventricular depolarization is a premature ventricular contraction (PVC) depolarization based on the intervals from the maximum slope point to the minimum slope point satisfying the one or more slope criteria; and
determine a PVC detection quantification for the patient based on the determinations that the plurality of ventricular depolarizations are PVCs; and
communication circuitry positioned within the housing and configured to transmit data comprising the PVC detection quantification determined by the processing circuitry via a network; and
a server configured to:
receive the data comprising the PVC detection quantification via the network; and
generate an output to a user computing device based on the PVC detection quantification.

27. The medical system of claim 26, wherein, to determine that the intervals from the maximum slope point to the minimum slope point satisfy the one or more slope criteria, the processing circuitry is configured to:
compare the intervals to each other;
determine a respective comparison metric value for each of the comparisons; and
determine whether the comparison metric values satisfy the one or more slope criteria.

28. The medical system of claim 27, wherein, to determine that the comparison metric values satisfy the one or more slope criteria, the processing circuitry is configured to:
determine that a first comparison metric for the comparison of the preceding adjacent ventricular depolarization to the subsequent adjacent ventricular depolarization satisfies a similarity criterion; and
determine that a second comparison metric for the comparison of the preceding adjacent ventricular depolarization to the current ventricular depolarization and a third comparison metric for the comparison of the subsequent adjacent ventricular depolarization to the current ventricular depolarization satisfy a dissimilarity criterion.

29. The medical system of claim 21, wherein the insertable cardiac monitor further comprises sensing circuitry within the housing and coupled to the plurality of electrodes, the sensing circuitry configured to provide a digitized version of the cardiac electrogram to the processing circuitry, wherein the processing circuitry is further configured to determine a respective window having a predetermined number of samples of the digitized version of the cardiac electrogram for each of the plurality of depolarizations, and for each of the plurality ventricular depolarizations as the current ventricular depolarization:
determine a correlation value between the samples of the windows for each pairing of one of the preceding adjacent ventricular depolarization, the current ventricular depolarization, and the subsequent adjacent ventricular depolarization and another of the preceding adjacent ventricular depolarization, the current ventricular depolarization, and the subsequent adjacent ventricular depolarization;
determine that the correlation values satisfy one or more correlation criteria; and
determine that the current ventricular depolarization is a PVC depolarization based on the correlation values satisfying the one or more correlation criteria.

* * * * *